US012806055B2

(12) United States Patent
Levering et al.

(10) Patent No.: US 12,806,055 B2
(45) **Date of Patent: *Nov. 24, 2026**

(54) DEVICES AND METHODS FOR MAINTAINING A PATENT DUCTUS ARTERIOSUS

(71) Applicant: STARLIGHT CARDIOVASCULAR, INC., San Diego, CA (US)

(72) Inventors: Vrad W. Levering, Oakland, CA (US); Kathryn A. Olson, San Diego, CA (US); Beverly T. Tang, La Jolla, CA (US); Mark S. Juravic, Encinitas, CA (US)

(73) Assignee: Starlight Cardiovascular, Inc., San Diego, CA (US)

(*) Notice: Subject to any disclaimer, the term of this patent is extended or adjusted under 35 U.S.C. 154(b) by 0 days.

This patent is subject to a terminal disclaimer.

(21) Appl. No.: 18/912,540

(22) Filed: Oct. 10, 2024

(65) Prior Publication Data

US 2025/0032291 A1 Jan. 30, 2025

Related U.S. Application Data

(62) Division of application No. 17/463,782, filed on Sep. 1, 2021, now Pat. No. 12,150,877.

(Continued)

(51) Int. Cl.
*A61F 2/07* (2013.01)
*A61F 2/06* (2013.01)
(Continued)

(52) U.S. Cl.
CPC ................ *A61F 2/966* (2013.01); *A61F 2/06* (2013.01); *A61F 2/07* (2013.01);
(Continued)

(58) Field of Classification Search
CPC .... A61F 2/966; A61F 2/06; A61F 2/07; A61F 2/962; A61F 2/90; A61F 2002/9511;
(Continued)

(56) References Cited

U.S. PATENT DOCUMENTS

| | | | |
|---|---|---|---|
| 5,261,878 | A | 11/1993 | Galindo |
| 5,741,333 | A | 4/1998 | Frid |

(Continued)

FOREIGN PATENT DOCUMENTS

| | | | |
|---|---|---|---|
| CA | 2261044 | A1 | 1/1998 |
| DE | 102014115337 | A1 | 4/2016 |
| EP | 3254648 | A1 | 12/2017 |

OTHER PUBLICATIONS

Akay E, Işik O, Engin AY, Çakr V. Stage 1 hybrid palliation of hypoplastic left heart syndrome: an initial experience in pulmonary trunk approach, procedural modifications, and complication management. Turk J Med Sci. Oct. 24, 2019;49(5):1374-1380. (Year: 2019).*

(Continued)

*Primary Examiner* — Tan-Uyen T Ho
*Assistant Examiner* — Osama Nemer
(74) *Attorney, Agent, or Firm* — Aurora Consulting LLC; Tiffany Miller; Ashley Sloat

(57) ABSTRACT

Methods for maintaining a patent ductus arteriosus in a pediatric patient include deploying a first end of a self-expanding stent at a first end of a lumen defined by a ductus arteriosus; anchoring at least a portion of a first flange of the first end of the stent such that the first flange at least partially circumferentially covers one of: a pulmonary artery ostium or an aortic ostium; deploying a second end of the stent, such that a stent body covers an entire length of the lumen defined by the ductus arteriosus; and anchoring a least a portion of a second flange of the second end of the stent such that the
(Continued)

second flange at least partially circumferentially covers the other of the pulmonary artery ostium or the aortic ostium.

8 Claims, 21 Drawing Sheets

Related U.S. Application Data

(60) Provisional application No. 63/073,819, filed on Sep. 2, 2020.

(51) Int. Cl.
*A61F 2/966* (2013.01)
*A61F 2/95* (2013.01)
*A61F 2/962* (2013.01)

(52) U.S. Cl.
CPC ....... *A61F 2002/9511* (2013.01); *A61F 2/962* (2013.01); *A61F 2210/0004* (2013.01)

(58) Field of Classification Search
CPC ........ A61F 2210/0004; A61F 2230/001; A61F 2230/0054; A61F 2250/0039; A61F 2250/0082
See application file for complete search history.

(56) References Cited

U.S. PATENT DOCUMENTS

| | | | | |
|---|---|---|---|---|
| 5,827,268 | A | 10/1998 | Laufer | |
| 6,336,938 | B1 | 1/2002 | Kavteladze et al. | |
| 6,623,518 | B2 | 9/2003 | Thompson et al. | |
| 6,814,746 | B2 | 11/2004 | Thompson et al. | |
| 7,527,644 | B2 | 5/2009 | Mangiardi et al. | |
| 7,731,741 | B2 | 6/2010 | Eidenschink | |
| 7,731,742 | B2 | 6/2010 | Schlick et al. | |
| 7,763,064 | B2 | 7/2010 | Pinchasik | |
| 8,414,635 | B2 | 4/2013 | Hyodoh et al. | |
| 8,579,958 | B2 | 11/2013 | Kusleika | |
| 9,101,504 | B2 | 8/2015 | Tippett et al. | |
| 9,259,336 | B2 | 2/2016 | Schaeffer et al. | |
| 9,408,952 | B2 * | 8/2016 | Sudhir | A61L 31/06 |
| 9,480,559 | B2 | 11/2016 | Vidlund et al. | |
| 10,092,429 | B2 | 10/2018 | Krolik et al. | |
| 10,568,781 | B2 | 2/2020 | Noel | |
| 10,932,786 | B2 | 3/2021 | McNamara et al. | |
| 11,246,706 | B2 | 2/2022 | Dale et al. | |
| 11,911,305 | B2 | 2/2024 | Smith et al. | |
| 2003/0135266 | A1 * | 7/2003 | Chew | A61F 2/91 623/1.16 |
| 2004/0220585 | A1 | 11/2004 | Nikolchev | |
| 2006/0111771 | A1 | 5/2006 | Ton et al. | |
| 2006/0265056 | A1 | 11/2006 | Nguyen et al. | |
| 2007/0055358 | A1 | 3/2007 | Krolik et al. | |
| 2009/0062839 | A1 | 3/2009 | Kurrus | |
| 2009/0099592 | A1 | 4/2009 | Buiser et al. | |
| 2009/0306706 | A1 | 12/2009 | Osypka | |
| 2011/0295353 | A1 | 12/2011 | Harris et al. | |
| 2012/0316597 | A1 | 12/2012 | Fitz et al. | |
| 2014/0277119 | A1 | 9/2014 | Akpinar | |
| 2015/0045881 | A1 | 2/2015 | Lim | |
| 2015/0119931 | A1 | 4/2015 | Amplatz et al. | |
| 2015/0127082 | A1 | 5/2015 | Sudhir et al. | |
| 2015/0374486 | A1 | 12/2015 | Dickinson et al. | |
| 2016/0120550 | A1 | 5/2016 | McNamara et al. | |
| 2017/0340433 | A1 | 11/2017 | Berra et al. | |
| 2018/0049859 | A1 | 2/2018 | Stoppenhagen et al. | |
| 2018/0049892 | A1 | 2/2018 | Henkes et al. | |
| 2018/0272044 | A1 | 9/2018 | Hossainy et al. | |
| 2019/0038393 | A1 | 2/2019 | Banco et al. | |
| 2019/0060052 | A1 * | 2/2019 | Harrison | A61F 2/915 |
| 2019/0083076 | A1 | 3/2019 | Alanbaei | |
| 2020/0093620 | A1 | 3/2020 | Fischer et al. | |
| 2020/0188098 | A1 | 6/2020 | Alkhatib et al. | |
| 2020/0254228 | A1 | 8/2020 | Taft et al. | |
| 2020/0323667 | A1 | 10/2020 | Garcia Torres et al. | |
| 2020/0391016 | A1 * | 12/2020 | Passman | A61F 2/2475 |
| 2021/0228386 | A1 | 7/2021 | Sachar et al. | |

OTHER PUBLICATIONS

Akay, Emrah et al. article titled “Stage 1 hybrid palliation of hypoplastic left heart syndrome: an initial experience in pulmonary trunk approach, procedural modifications, and complication management,” Turkish Journal of Medical Sciences, Research Article, doi:10.3906/sag-1903-143, pp. 1374-1380
International Preliminary Report on Patentability re PCT/US2022/033872 dated Dec. 14, 2023 (14 pages).
International Search Report dated Nov. 17, 2022 re PCT/US22/33872 (5 pages).
International Search Report dated Dec. 11, 2023 re PCT/US23/68516 (2 pages).
Written Opinion dated Nov. 17, 2022 re PCT/US22/33872 (13 pages).
Written Opinion dated Dec. 11, 2023 re PCT/US23/68516 (7 pages).
Extended European Search Report re 22825862.0-1113 / 4351486 PCT/US2022033872 dated Mar. 31, 2025 (13 pages).

* cited by examiner

DEVICES AND METHODS FOR MAINTAINING A PATENT DUCTUS ARTERIOSUS

CROSS-REFERENCE TO RELATED APPLICATIONS

This application is a divisional of U.S. NonProvisional patent application Ser. No. 17/463,782, filed Sep. 1, 2021, which claims the priority benefit of U.S. Provisional Patent Application Ser. No. 63/073,819, filed Sep. 2, 2020, the contents of each of which are herein incorporated by reference in their entirety.

INCORPORATION BY REFERENCE

All publications and patent applications mentioned in this specification are herein incorporated by reference in their entirety to the same extent as if each individual publication or patent application was specifically and individually indicated to be incorporated by reference.

FIELD

This application relates to the field of cardiovascular stents, in particular, stents designed for the ductus arteriosus and methods for maintaining a patent ductus arteriosus.

BACKGROUND

The technical challenges faced by pediatric cardiovascular physicians (surgeons and interventionalists alike) have long been ignored, forcing them to use devices designed for adults and different conditions to treat ailing babies with very specific anatomical considerations. One such case is in the sustained opening of the ductus arteriosus, a natural conduit that exists in all newborns but closes shortly after birth. In certain congenital heart defects, it is crucial to maintain ductus patency for the newborn to survive without surgical intervention. Although stent-like devices exist to address numerous cardiovascular conditions, there is nothing designed specifically to maintain patency of the ductus arteriosus in neonates that is commercially available in the United States. Consequently, reintervention, morbidity, and mortality associated with the current standard of care is unacceptably high. Pediatric interventional cardiologists currently repurpose adult coronary artery stents for the ductus, and all-cause ductus reintervention is 47% (Glatz 2018).

Accordingly, there exists a need for new devices and methods for maintaining a patent ductus arteriosus.

SUMMARY

One aspect of the present disclosure is directed to a method of maintaining a patent ductus arteriosus in a pediatric patient. In some embodiments, the method includes deploying a first end of a self-expanding stent at a first end of a lumen defined by a ductus arteriosus; anchoring at least a portion of a first flange of the first end of the stent such that the first flange at least partially circumferentially covers one of: a pulmonary artery ostium or an aortic ostium; deploying a second end of the stent, such that a stent body covers an entire length of the lumen defined by the ductus arteriosus; and anchoring a least a portion of a second flange of the second end of the stent such that the second flange at least partially circumferentially covers the other of the pulmonary artery ostium or the aortic ostium.

In some embodiments, the method includes deploying the stent body segment by segment to control a spacing between adjacent segments to ensure coverage of the entire length of the lumen defined by the ductus arteriosus.

In some embodiments, the stent body has two or fewer connections between adjacent rings.

In some embodiments, the stent body has three or fewer connections between adjacent rings.

In some embodiments, the stent body has zero or one connection between adjacent rings.

In some embodiments, the method includes conforming the stent body to a curvature of the ductus arteriosus.

In some embodiments, at least a portion of a diameter of the lumen defined by the ductus arteriosus is about 4 mm to about 8 mm and an outer diameter of the stent body is about 3 mm to about 4.5 mm.

In some embodiments, at least a portion of the diameter of the lumen defined by the ductus arteriosus is about 5 mm to about 10 mm and an outer diameter of the stent body is about 5 mm to about 9 mm.

In some embodiments, at least a portion of a diameter of the lumen defined by the ductus is about 5 mm to about 9 mm and an outer diameter of the stent body is about 6 mm to about 10 mm.

In some embodiments, a segment comprises one of: a ring or a ring and a connector.

In some embodiments, the method includes administering a prostaglandin to the pediatric patient to dilate a lumen defined by the ductus arteriosus of the pediatric patient.

In some embodiments, at least a portion of a diameter of the lumen defined by the ductus arteriosus is about 20% to about 140% larger than an outer diameter of the stent body.

In some embodiments, the method includes maintaining the lumen defined by the ductus arteriosus patent for one month or longer.

In some embodiments, the method includes preventing the at least a portion of the second flange of the second end of the stent from extending into either the pulmonary artery or the aorta by more than about 2 mm.

In some embodiments, deploying includes using a microcatheter.

Another aspect of the present disclosure is directed to a method of maintaining a patent ductus arteriosus in a pediatric patient to increase a pulmonary circulation of the pediatric patient. In some embodiments, the method includes deploying a distal end of a self-expanding stent at a first end of a lumen defined by a ductus arteriosus; anchoring at least a portion of a distal flange of the distal end of the stent such that the distal flange at least partially circumferentially covers a pulmonary artery ostium; deploying a proximal end of the stent, such that a stent body covers an entire length of the lumen defined by the ductus arteriosus; and anchoring a least a portion of a proximal flange of the proximal end of the stent such that the proximal flange at least partially circumferentially covers an aortic ostium.

In some embodiments, the method further includes administering a prostaglandin to the pediatric patient to dilate the lumen defined by the ductus arteriosus of the pediatric patient.

In some embodiments, anchoring further includes stretching the stent body to cover the entire length of the ductus arteriosus.

In some embodiments, covering the entire length of the ductus arteriosus includes supporting a tissue of the ductus arteriosus along its length.

In some embodiments, deploying includes using a micro-catheter.

In some embodiments, the method further includes preventing the at least a portion of the distal flange of the distal end of the stent from extending into the pulmonary artery by more than about 2 mm.

In some embodiments, the method further includes preventing the at least a portion of the proximal flange of the proximal end of the stent from extending into the aorta by more than about 2 mm.

In some embodiments, at least a portion of a diameter of the lumen defined by the ductus arteriosus is about 40% to about 140% larger than an outer diameter of the stent body.

In some embodiments, at least a portion of a diameter of the lumen defined by the ductus arteriosus is about 20% to about 100% larger than an outer diameter of the stent body.

In some embodiments, the method further includes maintaining the lumen defined by the ductus arteriosus patent for one month or longer while removing the prostaglandin administration.

In some embodiments, at least a portion of a diameter of the lumen defined by the ductus arteriosus is about 4 mm to about 8 mm and an outer diameter of the stent body is about 3 mm to about 4.5 mm.

Another aspect of the present disclosure is directed to a method of maintaining a patent ductus arteriosus in a pediatric patient to increase a systemic circulation of the pediatric patient. In some embodiments, the method further includes deploying a distal end of a self-expanding stent at a first end of a lumen defined by a ductus arteriosus; anchoring at least a portion of a distal flange of the distal end of the stent such that the distal flange at least partially circumferentially covers an aortic ostium; deploying a proximal end of the stent, such that a stent body covers an end-to-end length of the lumen defined by the ductus arteriosus; and anchoring a least a portion of a proximal flange of the proximal end of the stent such that the proximal flange at least partially circumferentially covers a pulmonary artery ostium.

In some embodiments, the method further includes administering a prostaglandin to the pediatric patient to dilate the lumen defined by the ductus arteriosus of the pediatric patient.

In some embodiments, covering the end-to-end length of the lumen defined by the ductus arteriosus further comprises ensuring that the lumen defined by the ductus arteriosus remains patent for at least one month.

In some embodiments, anchoring further includes stretching the stent body to cover the entire length of the ductus arteriosus.

In some embodiments, covering the entire length of the ductus arteriosus includes supporting a tissue of the ductus arteriosus along its length.

In some embodiments, the method further includes preventing the at least a portion of the proximal flange of the proximal end of the stent from extending into the pulmonary artery by more than about 2 mm.

In some embodiments, the method further includes preventing the at least a portion of the distal flange of the distal end of the stent from extending into the aorta by more than about 2 mm.

In some embodiments, at least a portion of a diameter of the lumen defined by the ductus arteriosus is about 40% to about 140% larger than an outer diameter of the stent body.

In some embodiments, at least a portion of a diameter of the lumen defined by the ductus arteriosus is about 20% to about 100% larger than an outer diameter of the stent body.

In some embodiments, at least a portion of a diameter of the lumen defined by the ductus is about 5 mm to about 9 mm and an outer diameter of the stent body is about 6 mm to about 10 mm.

Another aspect of the present disclosure is directed to a method of maintaining a patent ductus arteriosus in a pediatric patient. In some embodiments, the method includes advancing a delivery system through a ductus arteriosus to an ostium of an adjacent artery; deploying a first end of a self-expanding stent at a first end of a lumen defined by a ductus arteriosus; deploying a stent body of the stent segment by segment to control a spacing between adjacent segments to ensure coverage of an entire length of the lumen defined by the ductus arteriosus; and deploying a second end of the stent at a second end of the lumen defined by the ductus arteriosus, such that the stent body covers the entire length of the lumen defined by the ductus arteriosus.

In some embodiments, the stent body has two or fewer connections between adjacent rings.

In some embodiments, the stent body has three or fewer connections between adjacent rings.

In some embodiments, the stent body has zero or one connection between adjacent rings.

In some embodiments, the method includes conforming the stent body to a curvature of the ductus arteriosus.

In some embodiments, at least a portion of a diameter of the lumen defined by the ductus arteriosus is about 4 mm to about 8 mm and an outer diameter of the stent body is about 3 mm to about 4.5 mm.

In some embodiments, at least a portion of a diameter of the lumen defined by the ductus is about 5 mm to about 9 mm and an outer diameter of the stent body is about 6 mm to about 10 mm.

In some embodiments, a segment comprises one of: a ring or a ring and a connector.

In some embodiments, the method includes administering a prostaglandin to the pediatric patient to dilate a lumen defined by the ductus arteriosus of the pediatric patient.

In some embodiments, at least a portion of a diameter of the lumen defined by the ductus arteriosus is about 20% to about 140% larger than an outer diameter of the stent body.

In some embodiments, at least a portion of a diameter of the lumen defined by the ductus arteriosus is about 20% to about 100% larger than an outer diameter of the stent body.

In some embodiments, the method includes maintaining the lumen defined by the ductus arteriosus patent for one month or longer.

In some embodiments, the method includes preventing the at least a portion of the second flange of the second end of the stent from extending into either the pulmonary artery or the aorta by more than about 2 mm.

BRIEF DESCRIPTION OF THE DRAWINGS

The novel features of the invention are set forth with particularity in the claims that follow. A better understanding of the features and advantages of the present invention will be obtained by reference to the following detailed description that sets forth illustrative embodiments, in which the principles of the invention are utilized, and the accompanying drawings of which:

Figure 1A:
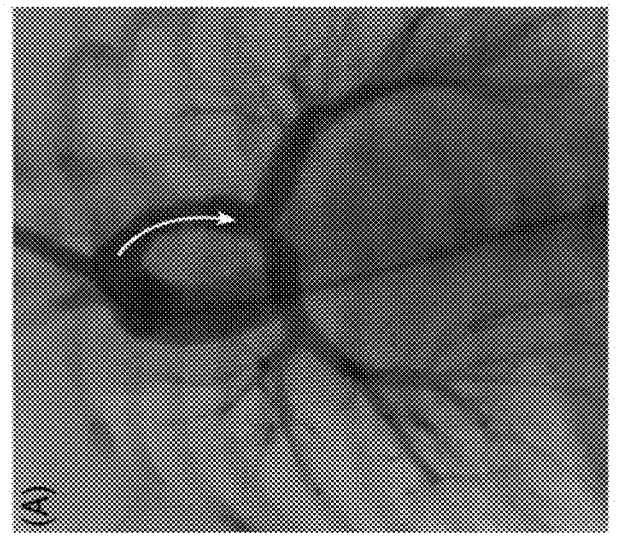
FIGS. 1A-1C show angiographic examples of various ductus anatomies.

The illustrated embodiments are merely examples and are not intended to limit the disclosure. The schematics are drawn to illustrate features and concepts and are not necessarily drawn to scale.

DETAILED DESCRIPTION

The foregoing is a summary, and thus, necessarily limited in detail. The above-mentioned aspects, as well as other aspects, features, and advantages of the present technology will now be described in connection with various embodiments. The inclusion of the following embodiments is not intended to limit the disclosure to these embodiments, but rather to enable any person skilled in the art to make and use the contemplated invention(s). Other embodiments may be utilized, and modifications may be made without departing from the spirit or scope of the subject matter presented herein. Aspects of the disclosure, as described and illustrated herein, can be arranged, combined, modified, and designed in a variety of different formulations, all of which are explicitly contemplated and form part of this disclosure.

As used herein, a "user" may include, but should not be limited to, a physician, assistant, doctor, nurse, interventionalist, healthcare provider, technician, radiologist, or the like.

As used herein, a "patient" may include, but not be limited to, a fetus, neonate, pediatric, toddler, pre-mature baby, baby, or the like.

As used herein, "ductus" and "ductus arteriosus" may be used interchangeably.

In some embodiments, as used herein, "an entire length of the ductus" may be measured from aorta ostium to pulmonary artery ostium, based on anatomical imaging, measured from a first ductal end (e.g., at the aorta) to a second ductal end (e.g., at the pulmonary artery), measured along the outer edge of the ductus curvature, measured along the inner edge of the ductus curvature, measured through the centerline of the ductus curvature, or the like.

As used herein, "proximal" and "distal" depend on the approach taken with a delivery system. For example, if approaching the ductus from the aorta, then the pulmonary artery may be considered to be distal with respect to the aorta and delivery system. If approaching the ductus from the pulmonary artery, then the aorta may be considered to be distal with respect to the pulmonary artery and delivery system. As such, in some cases, first and second ends are used to replace proximal and distal terminology to illustrate the interchangeability of these terms and their dependency on the type of procedure being performed.

Described herein are various ductus arteriosus stent embodiments and methods for delivering such stents. These embodiments are specifically designed to address the challenges facing treating physicians, including a right-sized delivery system, end-to-end annular coverage of the ductus arteriosus, navigation and deployment through tortuous ductus anatomy, and precise placement to avoid stent protrusion into the aorta and pulmonary arteries. Embodiments of the stents and their method of delivery and placement that are designed and tested specifically for this purpose will decrease reinterventions, morbidity, vasospasm, and potentially mortality for patients with ductal-dependent circulation.

Innovative embodiments of stents are described herein. One embodiment makes use of various stent embodiments having segments that allow a physician to choose exactly how many segments to deploy to cover the entire length of the ductus arteriosus. Additional various stent embodiments configured for placement in a ductus arteriosus include pre-shaped flanges, flared, or cuffed ends, located at a distal and/or proximal end of the stent that anchor the stent at one or both ends within the ductus arteriosus, thus ensuring complete coverage of the length of the ductus without a risk of stent movement, regardless of the stent length and ductus anatomy. It will be appreciated that a segmented stent may also incorporate flanges on one or both ends of a stent body or that any of the flanged stents described herein may be configured with flanges. In an embodiment of the present invention, the proximal end may comprise a flange and the distal end may comprise a flange with an appropriate number of internal segment rings coupled therebetween. Alternatively, a segmented stent may not comprise flanged ends or may only include one flanged end.

Approximately 2,000 babies are born in the US yearly that could benefit from a ductus arteriosus stent, categorized into two groups: patients with ductal-dependent pulmonary circulation and patients with ductal-dependent systemic circulation.

Patients with ductal-dependent pulmonary circulation are typically treated with Modified Blalock-Taussig shunts (MBTS), a surgical procedure where the chest is opened, the neonate is put on cardiopulmonary bypass, and a plastic conduit is implanted to provide flow to the systemic and pulmonary circulations. MBTS carry a 7.2% risk of mortality and 13.1% risk of morbidity in the U.S., despite the quality of care that our highly skilled pediatric cardiothoracic surgeons provide. Alternatively, ductal stenting has resulted in similar or reduced mortality over MBTS and provides ductal-dependent pulmonary circulation without the need for cardiopulmonary bypass, which can have deleterious effects on brain development. Stenting the ductus with "repurposed" coronary stents that are currently available carries a 47% rate of reintervention. Reintervention rates are higher when a portion of the stent extends into the pulmonary artery either partially or fully jailing one of the branch pulmonary arteries, which occurs in 21.9% of ductus stenting cases with "repurposed" coronary stents. A stent and delivery system designed and tested for maintaining ductus arteriosus patency could move patients from open surgery to a less invasive approach, with reduced mortality compared to MBTS and fewer reinterventions compared to stenting with "repurposed" coronary stents.

Patients with ductal-dependent systemic circulation typically have Hypoplastic Left Heart Syndrome (HLHS). The first procedure in a three-stage palliation for HLHS is typically performed in the first two weeks of life, and a hybrid procedure which requires ductal stenting could prevent the need for putting these neonates on bypass. Some facilities have had good results with hybrid stage I palliation procedures, but results are inconsistent and challenges using "repurposed" stents in the ductus remain. The ductus arteriosus stents described herein could also address the HLHS patient population by modifying the stent diameter and addressing aortic impingement.

The current coronary stents that are repurposed for ductal stenting are all balloon-expandable, resulting in some limitations in radial force and foreshortening with balloon deployment. Balloon-expandable systems can also be very stiff on the distal end with the crimped stent loaded over the balloon material, making tracking through tortuous anatomy challenging. Also unsuccessfully, previously designed self-expanding stents that have sufficient flexibility to advance through the tortuous anatomy, while loaded in the delivery system, have been shown to have insufficient radial force or kink resistance to maintain an open lumen. In some embodiments, the stents described herein are made using Nitinol, which is self-expanding and can be tailored to have a sufficient radial force to maintain a patent ductus lumen. This radial force can be precisely dialed in during the design process and then maintained in manufacturing.

More specifically, issues with using repurposed stents in the ductus arteriosus include: 1) a lack of understanding of ductus tissue-stent interaction for selecting a stent with the proper radial force; 2) challenging measurement of the 3D ductus arteriosus with 2D angiography, making stent sizing difficult; 3) mechanical properties of the stent and delivery system change the ductus tortuosity and length, further complicating stent sizing (e.g., the stent may straighten the ductus or elongate the ductus); 4) difficulty in precise stent placement to prevent protrusion into surrounding arteries; 5) delivery systems are designed for adult vessels, risking damage to the smaller, vulnerable blood vessels from percutaneous access to placement location; 6) current delivery systems are not designed for the approach angles or deployment in tortuous ductus anatomies; and (7) at least for pulmonary dependent circulation, with balloon stents, a practitioner must choose the size of the stent that they'd like the ductus to be. For example, the stent cannot be too big (e.g., too large of an inner or outer diameter) or too much blood flow may go to lungs. In such a setting, the practitioner cannot use prostaglandins during the procedure to get the ductus to the right size (i.e., cannot estimate the size the ductus should be if it is dilated on prostaglandins). Further, this approach also has a much higher chance of vasospasm, which is very dangerous to the patient.

Stent embodiments described herein provide stents with optimized radial force for maintaining ductus arteriosus patency and novel features that address the length and placement challenges described above. The stents described herein ensure accurate delivery and placement as well as annular coverage over the entire length of a patient's ductus arteriosus, to maintain patency of the ductus, without interference with or substantial protrusion into the adjacent aorta or pulmonary artery. Protrusion into adjacent arteries often leads to additional surgeries to adjust and correct the placement of the stent.

Further, any of the stent embodiments described herein may be configured for delivery with a catheter or a microcatheter. Microcatheters offer distinct advantages for maintaining a patent ductus arteriosus. For example, microcatheters are more deliverable to access difficult anatomy compared to balloon mounted stents, and microcatheters enable smaller access sites. Further, as described elsewhere herein, an outer diameter of the stent needs to be about 3 mm to about 5 mm or about 6 mm to about 10 mm, based on the target patient population (e.g., ductal-dependent pulmonary or systemic circulation), but the stent also must have a sufficient radial resistive force to support the ductal tissue and maintain its patency. Accordingly, such self-expanding but sufficient radial force stents, as described herein, may use a microcatheter for delivery and deployment. In some embodiments, during distal anchoring end deployment, the microcatheter may extend, at least partially, into the adjacent aorta or pulmonary artery to ensure placement of the stent at the aorta ostium or pulmonary artery ostium, respectively.

In any of the embodiments or figures shown and/or described herein, a catheter or microcatheter may be used as part of a delivery system. Selection of a catheter or microcatheter may be used herein depending on physician preference, type of circulation desired (e.g., pulmonary vs. systemic), size of stent, size of the ductus arteriosus of the patient, etc.

Advantageously, embodiments of ductus arteriosus stents described herein are configured to precisely cover an annular region of the ductus arteriosus with a single stent to maintain patency while not inhibiting blood flow through adjacent arteries. The stents of the present invention, (various embodiments shown in FIGS. 2A-2G), can be positioned along the length of the ductus and also enable changes of the stent length during stent delivery and placement to ensure coverage of an entire length of the ductus. Any of the stent embodiments described herein are further configured to support the tissue of the ductus along its length to prevent closure of the ductus. If a portion of the ductal tissue is unsupported, the ductus will close resulting in at least a partial loss of blood circulation in the patient.

Figure 1B:
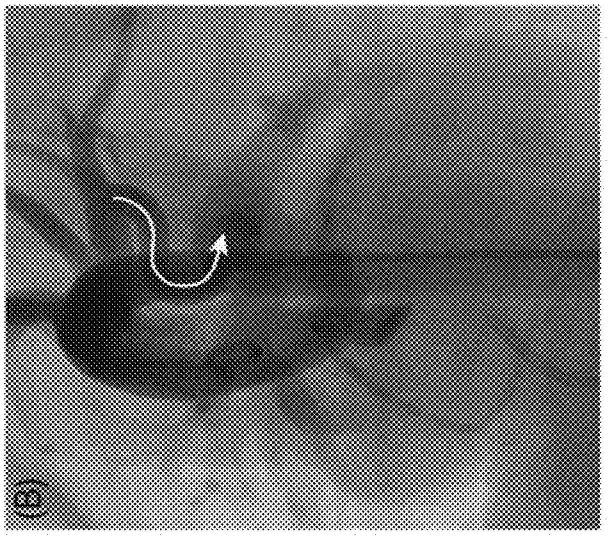
Figure 1C:
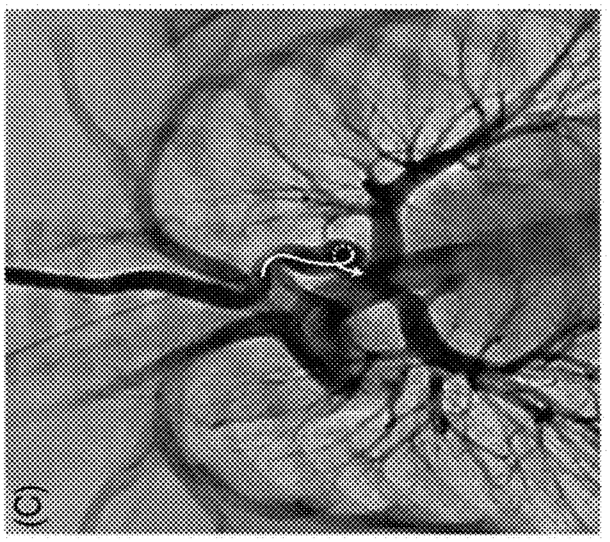

FIGS. 1A-1C illustrate various example anatomies of a patient's ductus arteriosus. FIG. 1A shows a substantially straight or linear, shorter ductus; FIG. 1B shows a more tortuous, longer ductus; and FIG. 1C shows a ductus having loops. The present invention advantageously provides systems and methods for stenting shorter to longer ductus arteriosus and including those having the tortuous, looping ductus. It will be appreciated that ductus lengths may range from about 8 to about 28 mm, but may also be shorter or longer depending on the patient's anatomy. Further, the devices and methods described herein may substantially conform to an anatomy of the ductus and reduce the likelihood of unnatural straightening or lengthening of the ductus.

Figure 2A:
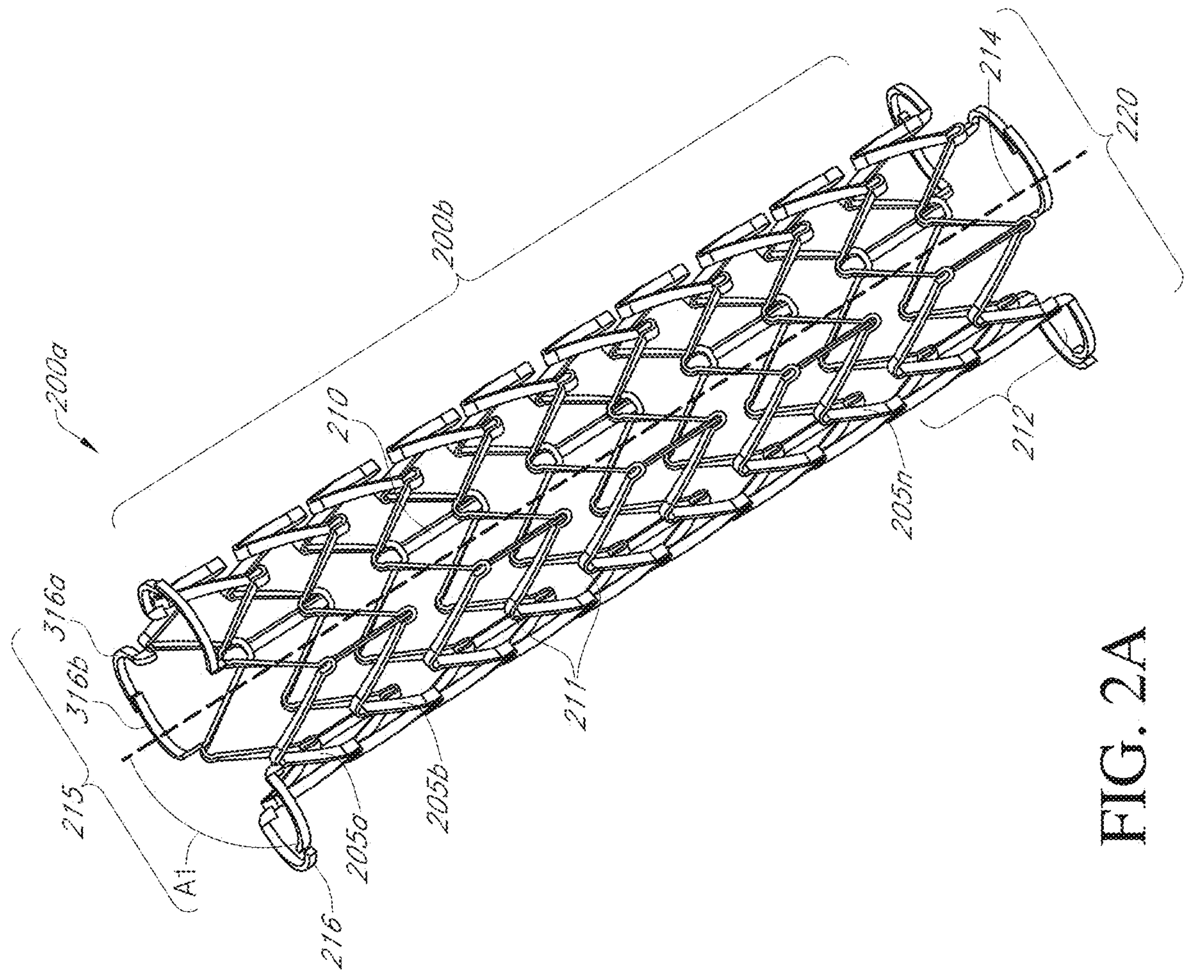
FIG. 2A shows one embodiment of a stent having semi-circular flanges extending substantially perpendicularly relative to the stent body.

FIG. 2A shows an embodiment of a stent 200*a* that can be utilized for maintaining a patent ductus arteriosus. As shown, the stent body 200*b* comprises a plurality of rings 205*a-n* that allow a user to controllably deploy a number of rings or segments in order to annularly cover the entire length of the ductus arteriosus. In some embodiments, as used herein, a segment comprises one or more rings connected via one or more connectors to form a connected unit. For example, as shown in FIG. 2A, a segment 212 may comprise two adjacent rings 205 connected by a connector 210. A stent body 200*b* may comprise one, one or more, or a plurality of segments 212. Similarly, a segment 212 may comprise one, one or more, or a plurality of rings 205 with or without connectors between some of the rings or between adjacent rings.

Further, it will be appreciated that the design and material selection of the stent allows for minor length adjustments, either longer or shorter, during placement or deployment. Advantageously, if the length of the ductus cannot be measured accurately or if the length of the ductus arteriosus does not accurately match an unconstrained length of the stent, the stent may be compressed or stretched to adjust for the length. For example, during deployment and/or positioning, a user may apply tension or compression to the microcatheter to either stretch or compress the stent, respectively. Further stent design, for example number of connectors between adjacent rings, material properties (e.g., Nitinol), and ring structure may also contribute to the stent's ability to be compressed or stretched during deployment and/or positioning. Additionally, or alternatively, the ductus may compress or stretch during stent delivery. As such, in certain implementations, only the stent is compressing or stretching; in certain others, only the ductus is compressing or stretching; in still certain other embodiments, both the stent and ductus are compressing or stretching during stent placement and/or delivery. As shown, each individual ring has one or more crowns 211. One or more adjacent crowns 211 are connected via connector 210, extending from one ring to another. In alternative embodiments, there may be three or fewer connectors between adjacent rings, two or fewer connectors between the adjacent rings, or zero or one connectors between adjacent rings. As will be appreciated by one of skill in the art, although crowns 211 are shown as the connection point between adjacent rings 205, adjacent rings 205 may be connected anywhere along their circumference or length. For stent embodiments having zero connectors, a delivery system may include multiple hubs such that each segment can be controllably deployed. In another embodiment, adjacent segments, for example a more proximal segment, may serve as the bumper for the next segment, or more distal segment.

Further, as one of skill in the art will appreciate, while each stent is shown having similar proximal and distal anchoring flanged ends, it is within the scope of the present disclosure to have differing proximal and distal flanged ends. For example, a flanged end of FIG. 2A may be combined with a flanged end of FIG. 2B or a flanged end of FIG. 2C may be combined with a flanged end of FIG. 2E or a flanged end of FIG. 2D may be combined with a flanged end of FIG. 2B, etc. Further, although the figures show both the proximal and distal ends of the stent as having flanged ends, one of skill in the art will appreciate that one end may be a flanged end while the other end may not include flanges and therefore may not be considered to be anchoring. In some embodiments, one or both flanged ends may be configured to prevent or reduce migration of the stent during deployment and/or while positioned in the patient for an extended period of time, as described elsewhere herein.

Figure 2B:
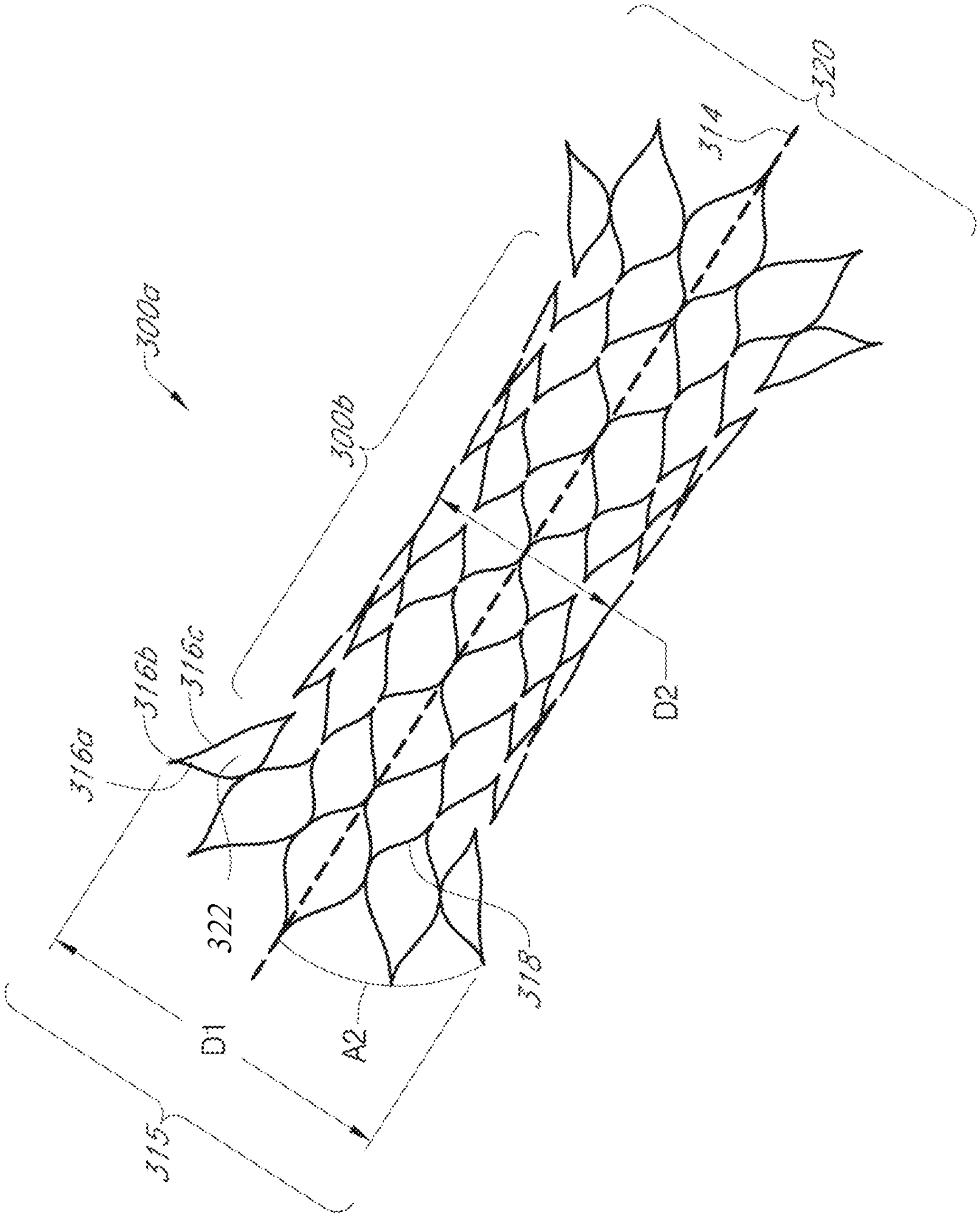
FIG. 2B shows another embodiment of a stent having a plurality of petal flanges extending from a first and second end of the stent.

In any of FIGS. 2A-2G but as shown in FIG. 2B, one or both flared ends may have a D1 of the terminal ring measured at the terminal crowns that is in the range of about 110% to 180% larger than an outer diameter D2 of the stent body; in the range of about 120% to about 170% larger than an outer diameter D2 of the stent body; in the range of about 130% to about 160% larger than an outer diameter D2 of the stent body; for example about 150%; about 155%; or about 160%.

The stent 200*a* of FIG. 2A also shows flanges 215, 220 on each of the first and second ends. These flanged ends 215, 220 are configured to contract while positioned within a delivery tube, and after placement in the ductus arteriosus, self-expand radially outward anchoring the stent 200*a* at both ends of the ductus arteriosus, situated between an aorta ostium and a pulmonary artery ostium. Advantageously, the flanged ends 215, 220 prevent the stent 200*a* from movement after placement as well as ensuring the stent 200*a* covers the entire length of the ductus arteriosus so that the ductus does not close (i.e., remains patent).

In the embodiment of FIG. 2A, flanged ends 215, 220 comprise one or more semi-circular flanges extending substantially perpendicularly relative to a centerline axis 214 of the stent body 200*b*. For example, the one or more semi-circular flanges 216 may have an angle A1 relative to the centerline axis 214 of the stent body 200*b* in a range of between about 45 degrees to about 120 degrees; about 60 degrees to about 110 degrees; about 70 degrees to about 110 degrees; about 80 degrees to about 100 degrees; substantially 90 degrees; etc. Each semi-circular flange may comprise a first connector 316*a* coupled to an adjacent or second connector 316*b*. At the flanged ends 215, 220, each connector 316*a*, 316*b* may extend from a crown 211 (e.g., could be adjacent crowns or spaced apart by one or more crowns) and couple therebetween to form the flange. The ends of the connectors 316*a*, 316*b* may be crimped, soldered, glued, welded, or otherwise coupled together. Alternatively, in one embodiment, they are not physically coupled but rather in close proximity to one another or overlapping along at least a portion of their length.

One key advantage of the various stent embodiments described herein, for example the stent 200*a* of FIG. 2A, is the reduction in connectors between rings of the stent, which vastly increases flexibility of the stent. This increased flexibility can greatly assist in the pushability and trackability of the stent as loaded in the catheter or microcatheter. Having separate segments 212 configured into a stent 200*a* instead of a single, or unibody, stent also decouples flexibility from many typical design levers for manipulating radial force (e.g., tubing wall thickness, strut width, strut length, etc.) and thereby facilitates design of a device that performs with both high flexibility and high radial force. Multiple segments 212 can be loaded and constrained in a single delivery system; however, the segments 212 can be sequentially and/or individually deployed using manual control of the delivery system, which may include a deployment sheath. This provides a user the ability to deploy as many segments 212 as required for the specific length of the patient's ductus arteriosus. Additionally, the user is able to intra-procedurally define the overall effective stent length and more easily accommodate anatomical changes of the ductus arteriosus generated by individual segment ring deployments or imprecise ductus measurement, as occurs commonly in tortuous ducts.

FIGS. 2B-2E and FIG. 2G show additional various embodiments of a stent configured for maintaining patency of the ductus. As shown in FIGS. 2A-2E and FIG. 2G, the flanged ends of the various stent embodiments are configured to anchor the stent at a first, or distal, end and a second, or proximal, end of the ductus, thus ensuring coverage over the entire length of a patient's ductus arteriosus, regardless of the overall length of the ductus or the stent. The flanged ends can be optionally configured to slightly compress at the ends of the ductus arteriosus; more specifically, the flanged ends are anchored at a first, or distal, ostium and at a second, or proximal, ostium and may slightly compress the ductus.

In this manner, the flanged ends also ensure that the entire length of the ductus is covered by the stent. It will be appreciated that the flanged ends of the stent do not substantially extend past the ostia and into the aorta and pulmonary artery. Additionally, the flanged ends at least partially circumferentially cover the ostia at both ends of the ductus arteriosus. Each stent is configured to cover the most common ductus lengths, for example, from about 8 mm to about 28 mm or from about 12 mm to about 24 mm, and are configured with diameters ranging from about 3 mm to about 10 mm, as is needed for ductal-dependent pulmonary (e.g., stent diameter of about 3 mm to about 5 mm) or systemic circulation (e.g., stent diameter of about 6 mm to about 10 mm).

Turning now to FIGS. 2B-2E and FIG. 2G in more detail, which show various stent designs that may be used as part of a method for maintaining patency of a ductus. As shown in FIG. 2B, flanged ends 315, 320 may extend radially away from a centerline axis 314 of the stent 300*a*. For example, flanged ends 315, 320 of stent 300*a* extend radially away from a centerline axis 314 by an angle A2 (measured between centerline axis 314 and terminal crown 316*b*) in the range of between about 40 degrees to about 90 degrees; about 45 degrees to about 85 degrees; about 50 degrees to about 80 degrees; about 55 degrees to about 75 degrees; substantially 65 degrees. As shown in FIG. 2B, each flanged end 315, 320 may comprise a terminal ring comprising a first strut 316*c* coupled to a second strut 316*a* joined at terminal crown 316*b*. An area of the terminal cell 322 defined by struts 316*a*, 316*c*; crown 316*b*; and adjacent ring 318 may be about 5% to about 75% or about 40% to about 60% larger, for example, than a cell in the stent body 300*b*.

In some embodiments, a large terminal cell area may not be desirable. Therefore, in some implementations, a terminal cell area may be substantially similar to or only marginally larger than (e.g., 1% to about 20% larger) a cell area defined by struts in the stent body.

Figure 2C:
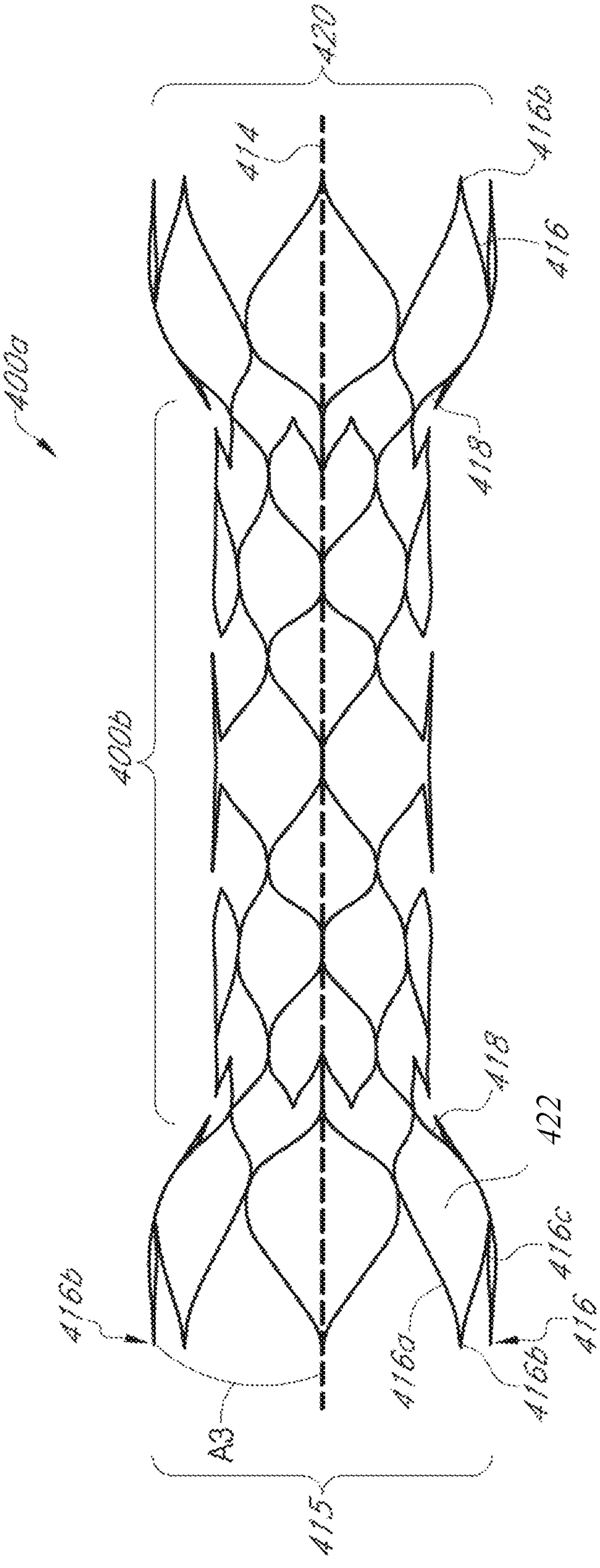
FIG. 2C shows another embodiment of a stent having a plurality of petal flanges extending from a first and second end of the stent.

FIG. 2C shows another embodiment of a stent 400*a* comprising stent body 400*b* and flanged ends 415, 420. The stent 400*a* of FIG. 2C is similar to the stent 300*a* in FIG. 2B in the structure of the stent body, but the flanged ends of stent 400*a* differ from the flanged ends of stent 300*a* in overall shape. For example, the flanged ends 415, 420 may have a cuff-like shape such that each terminal cell 422, defined by the terminal struts 416*a*, 416*c* and adjacent ring 418, is substantially equidistant from the centerline axis 414 as each terminal crown 416*b*. Flanged ends 415, 420 taper to the stent body 400*b* at adjacent rings 418, such that adjacent ring 418 has a smaller diameter than terminal ring 416 comprising terminal struts 416*a*, 416*c* and crown 416*b*. Said another way, flanged ends 415, 420 of stent 400*a* expand outwardly while the ends or terminal crowns 416*b* remain parallel to centerline axis 414 of stent body 400*b*. Further, flanged ends 415, 420 of stent 400*a* extend radially away from a centerline axis 414 by an angle A3 (measured between centerline axis 414 and crown 416*b*) in the range of between about 40 degrees to about 80 degrees; about 35 degrees to about 65 degrees; about 40 degrees to about 60 degrees; about 50 degrees to about 70 degrees; about 55 degrees to about 65 degrees; substantially 55 degrees; or substantially 60 degrees.

Figure 2D:
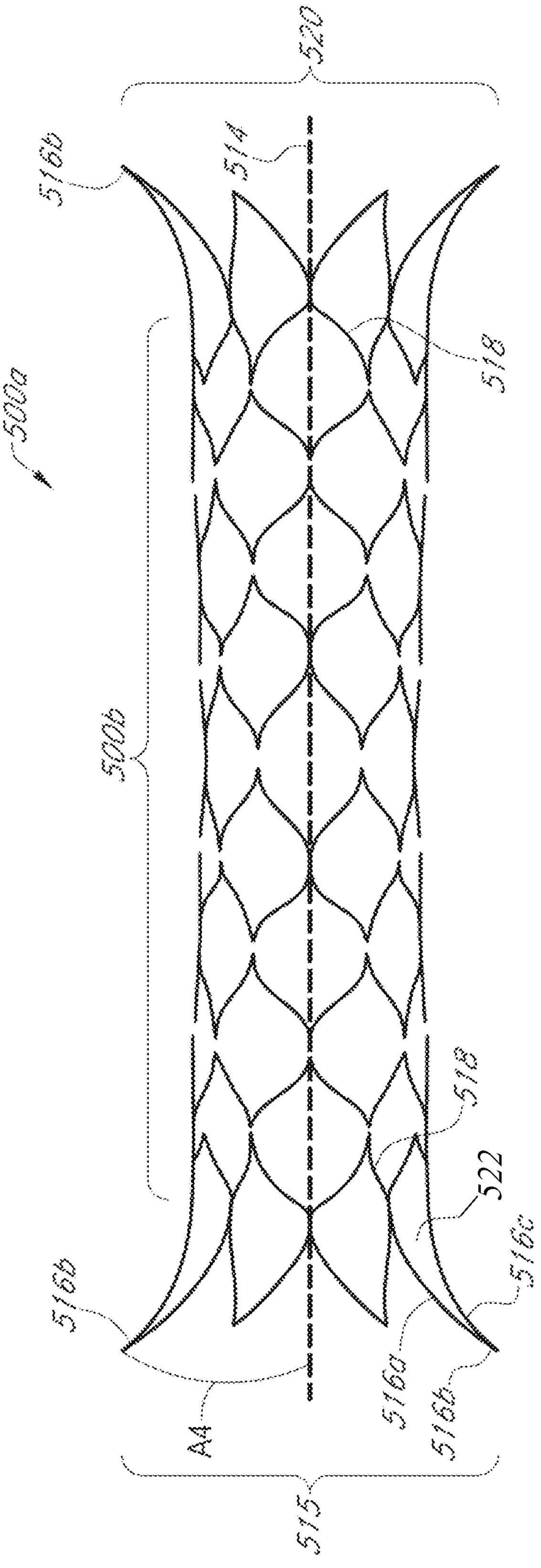
FIG. 2D shows another embodiment of a stent having a plurality of petal flanges extending from a first and second end of the stent.

FIG. 2D shows another embodiment of a stent 500*a* comprising stent body 500*b* and flanged ends 515, 520. The stent 500*a* of FIG. 2D is similar to the stent 400*a* of FIG. 2C in the structure of the stent body, but flanged ends of stent 500*a* differ from flanged ends of stent 400*a* in overall shape. Flanged ends 515, 520 of stent 500*a* also extend radially away from a centerline axis 514 by an angle A4 (measured between centerline axis 514 and terminal crown 516*b*) in the range of between about 30 degrees to about 60 degrees; about 25 degrees to about 65 degrees; about 35 degrees to about 55 degrees; about 45 degrees to about 55 degrees; about 40 degrees to about 70 degrees; substantially 45 degrees; or substantially 50 degrees. However, in the embodiment of FIG. 2D, each terminal cell 522, defined by the terminal struts 516*a*, 516*c* and adjacent ring 518, tapers (e.g., gradually or abruptly, for example along a substantially hyperbolic curve) to stent body 500*b*, such that adjacent ring 518 is substantially colinear with stent body 500*b* or substantially equidistant from centerline axis 514 as stent body 500*b*.

Figure 2E:
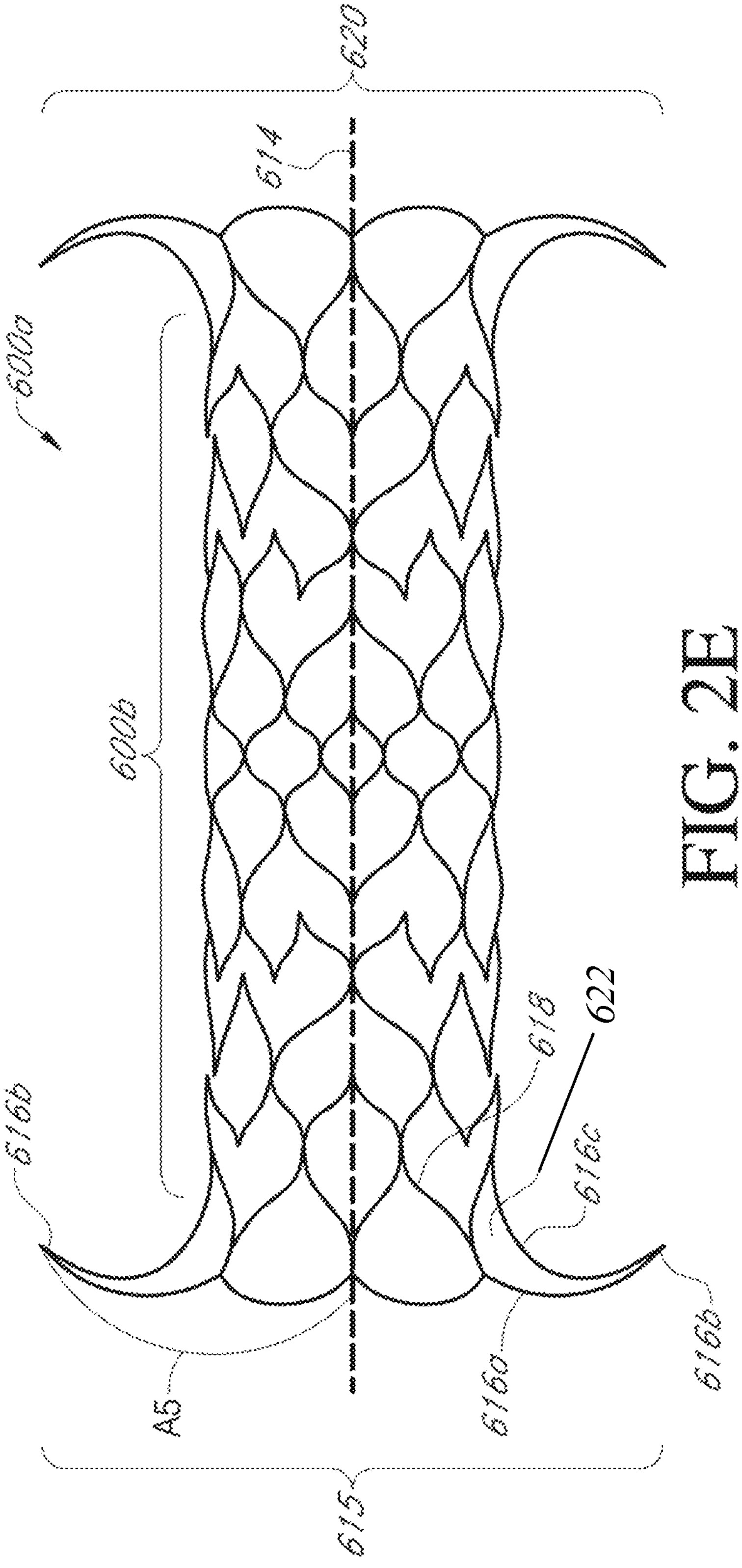
FIG. 2E shows another embodiment of a stent having a plurality of petal flanges extending substantially greater than 90 degrees relative to the stent body.

FIG. 2E shows another embodiment of a stent 600*a* comprising stent body 600*b* and flanged ends 615, 620. The stent 600*a* of FIG. 2E is similar to the stent 500*a* of FIG. 2D in the structure of the stent body, but flanged ends of stent 600*a* differ from flanged ends of stent 500*a* in overall shape. For example, each terminal cell 622, defined by the terminal struts 616*a*, 616*c* and adjacent ring 618, is substantially colinear with stent body 600*b* or substantially equidistant from the centerline axis 614 as stent body 600*b* along its length, but terminal crown 616*b* is substantially radially deflected from a centerline axis 614 of stent body 600*b*. Angle A5, measured between centerline axis 614 and terminal crown 616*b*, is in the range of between about 80 degrees to about 135 degrees; about 90 degrees to about 120 degrees; about 100 degrees to about 110 degrees; about 90 degrees to about 100 degrees; about 80 degrees to about 100 degrees; substantially 90 degrees; or substantially 100 degrees.

Figure 2F:
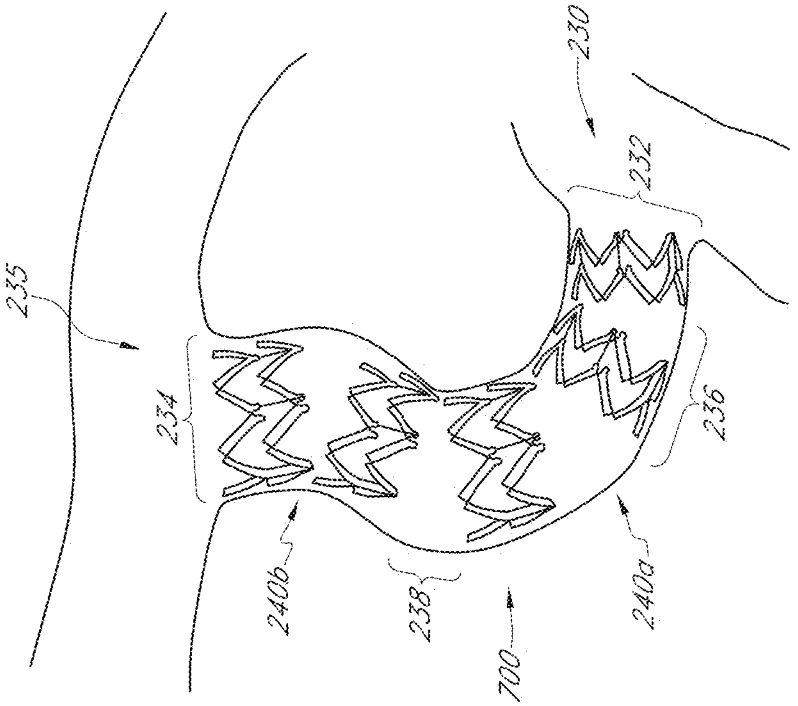
FIG. 2F shows another embodiment of a stent having one or zero connectors between adjacent segments for segmental delivery.
Figure 2G:
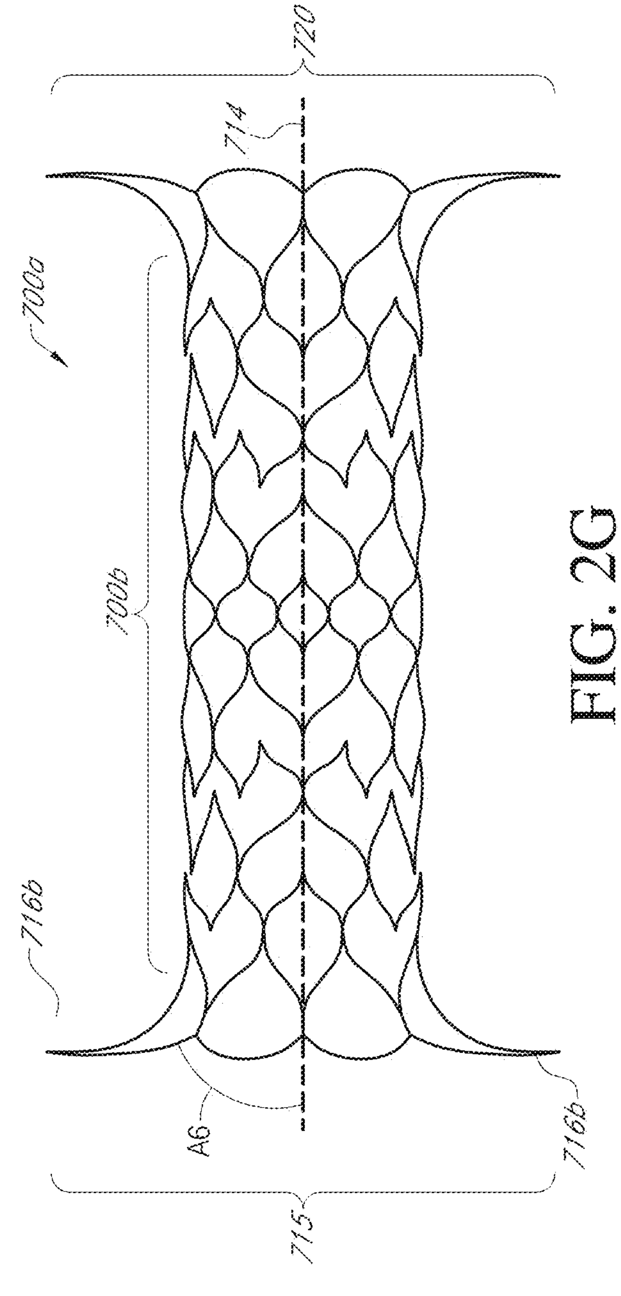
FIG. 2G shows another embodiment of a stent having a plurality of petal flanges extending about 90 degrees relative to the stent body.

FIG. 2G illustrates shows another embodiment of a stent 700*a* comprising stent body 700*b* and flanged ends 715, 720. The embodiment of FIG. 2G is similar to that of FIG. 2E, except that angle A6, measured between centerline axis 714 and terminal crown 716*b*, is in the range of between about 80 degrees to about 100 degrees; about 85 degrees to about 95 degrees; substantially 85 degrees or substantially 90 degrees or substantially 95 degrees.

In some embodiments, flanged ends may transition between the configuration shown in FIGS. 2B-2E, 2G during the delivery or positioning or deployment process, such that the flanged ends start at a first configuration and transition to one or more secondary configurations during use or during the stenting procedure or while positioned in the patient over time.

FIG. 2F illustrates a segmental stent placement in a patient's ductus arteriosus. Note that in this embodiment, stent 700 does not include, but could include, one or more flanged ends. As shown, stent 700 is placed between an aorta 230 and a pulmonary artery 235. Flanged ends of any of the stents shown and described elsewhere herein (not shown in FIG. 2F) may be anchored at the ostium 232 of the aorta 230 and the ostium 234 of the pulmonary artery 235. Also, an example showing the flexibility of the stent 700 can be appreciated in a curved ductus arteriosus where the stent 700 expands and covers curved regions 240*a*, 240*b*. However, even without one or more flanged ends, segmental delivery of stent 700 ensures end-to-end coverage of an entire length of the ductus to maintain patency. FIG. 2F further shows that segments 236 may be individually deployed along the length of the ductus. For example, as shown in FIG. 2F, adjacent rings either have zero or one to three connectors therebetween. Segment 236, as described elsewhere herein, includes a single ring or one or more rings connected by one, one to two, one to three, or one to four connectors therebetween. A distance 238 between adjacent segments 236 may either be increased or decreased during deployment of the stent 700 to adjust the stent 700 to a curvature of the ductus, to fully cover the ductus along its length, and/or to reduce or prevent unnatural straightening of the ductus during stenting. FIGS. 6A-6D describe this method of stent deployment in greater detail. In some embodiments, stents configured for segmental deployment may or may not have flanged ends. Similarly, any of the stents described herein may or may not be configured for segmental delivery, as described in FIGS. 6A-6D.

Advantageously, the stent embodiments described herein provide as-loaded flexibility on the delivery device, such as a catheter or microcatheter, due to connectors between rings having a narrow width. For example, struts within a stent ring may alternate in thickness such that the thinner struts may function similarly to connectors to provide additional flexibility to the stent, and thus the delivery system during advancement through the vasculature and/or stent deployment. For example, a width of each connector may be substantially similar to a width of one or more or a plurality of the stent struts. In some embodiments, a strut connector may be about 2% to about 30% or about 5% to about 30% or about 10% to 30% or up to 30% narrower than each stent strut. During delivery and placement of any of the stents described herein, the delivery device can partially deploy a first flanged end 215 and a subset of rings comprising the stent body at a distal end of the ductus first, which may be, for example, the distal end at the pulmonary artery or, in other embodiments, the distal end at the aorta. As an example, a first subset of about 50% of the rings may be deployed along with the flanged end that anchors to the pulmonary artery wall 235 at the ostium adjacent to the ductus. While deploying the second subset of the rings and the proximal flanged end, the delivery system is configured to receive tension from a user (e.g., an interventionist or surgeon). In this manner, the received tension compresses the length of the ductus arteriosus slightly and/or stretches the stent. The slight compression of the ductus length allows the user to compensate for inaccurate ductus length measurements, which are inherently imprecise due to two-dimensional measurements of a tortuous three-dimensional structure. More specifically, a determined overall length of the stent body may be slightly shorter than the length of a patient's ductus arteriosus, and the flanged ends that anchor at the ostia compress the ductus to be essentially equal to the shorter length. Importantly, the compressed length of the ductus, accomplished by the flanged ends and/or delivery method, ensure that any of the stent embodiments described herein completely extend the entire length of the ductus arteriosus to ensure that patency is maintained for about one week to about four weeks; about one month to about 4 months; about one month to about twelve months; about 2 months to about 6 months; etc.

Figure 3:
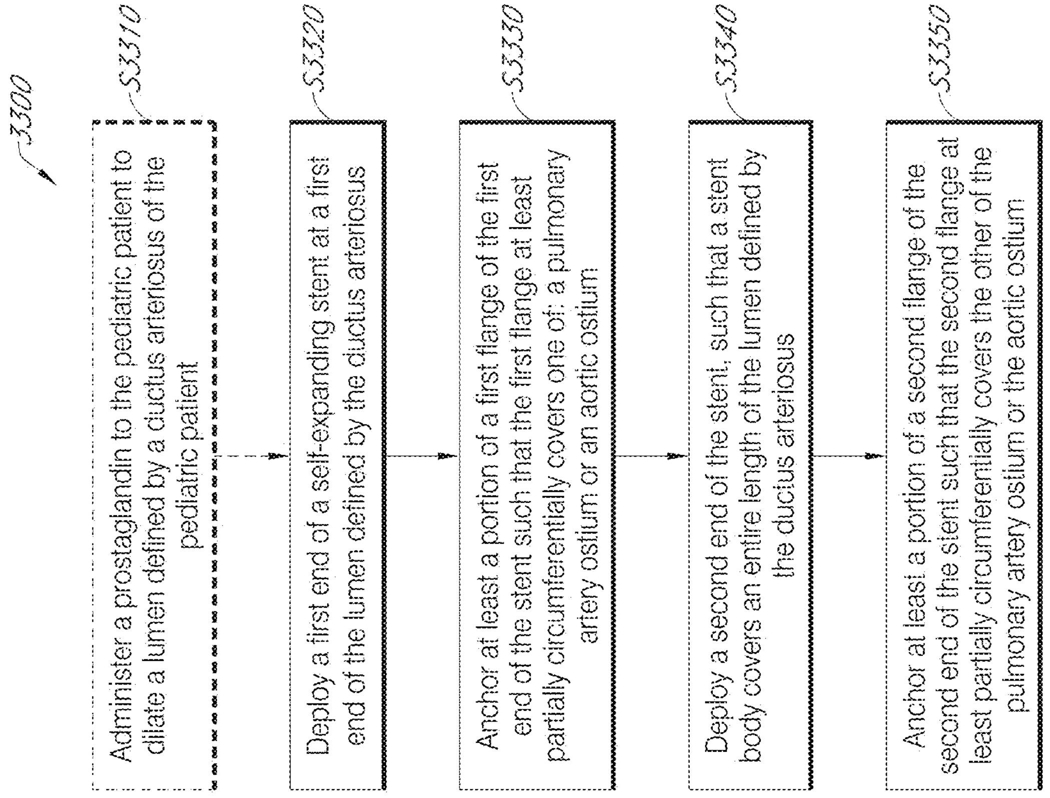
FIG. 3 shows a flow chart of a method of maintaining a patent ductus arteriosus in a pediatric patient.

FIG. 3 illustrates one embodiment of a method using a delivery system, for example including a catheter or microcatheter, to deliver and place any of the stent embodiments described herein in a ductus arteriosus of a patient. The method 3300 may include optionally administering a prostaglandin to the patient to dilate the ductus arteriosus, as shown at block S3310. Delivering a stent on prostaglandins significantly reduces the risk of vasospasm, a life-threatening situation for patients. While the ductus is enlarged, the delivery system is configured to constrain and deploy any of the stent embodiments described herein within the ductus arteriosus. At block S3320, at a first, or distal, end of the ductus arteriosus, a first, or distal, flanged end is released from the delivery system and radially expands until it approximately reaches the lumen as defined by the ductus arteriosus. At block S3330, at least a portion (e.g., one or more crowns, all or a portion of one or more cells, all or a portion of the terminal ring, etc.) of the expanded first flanged end anchors into the ductus lumen defining an ostium at either a pulmonary artery or an aorta depending upon the approach of the delivery system. As described herein, the anchored portion of the first flanged end may comprise any one or more of the features shown in FIGS. 2A-2G. The microcatheter retracts and deploys the stent body or individually deploys expandable segments or a subset of the segments of the stent body throughout the remaining length of the ductus arteriosus at block S3340. As discussed herein, each segment may include one or more rings that are coupled by one, one to two, one to three, or one to four connectors therebetween. When the second, or proximal, end of the ductus is reached, a second, or proximal, flanged end is released and expands, and at least a portion (e.g., one or more crowns, all or a portion of one or more cells, all or a portion of the terminal ring, etc.) of the flanged end anchors into the second, or proximal, end of the lumen as defined by the ductus arteriosus at block S3350. The anchored portion of the second flanged end may comprise any one or more of the features shown in FIGS. 2A-2G. It will be appreciated that the first and second flanged ends may be different configurations from one another. Further, the second end of the lumen is at the other end of the ductus arteriosus, which may be either the pulmonary artery or the aorta, depending upon the approach of the delivery system.

To ensure complete coverage of the entire length of the ductus arteriosus, a first subset of segments may be deployed, and the user may apply tension to the delivery system while deploying a second subset of segments at block S3340. The tension on the delivery system may compress the stent body, which may slightly compress the ductus arteriosus to effectively shorten the length ensuring that the stent extends completely from end to end. The first subset of segments deployed may comprise one or more segments, or up to about 50% of the total individual segments of the stent body.

In some embodiments, any of the methods described herein may further include accessing an access site (e.g., femoral, carotid, radial, brachial, etc.), for example using an introducer sheath; and navigating a guidewire through the sheath and into a ductus arteriosus of the patient. The ductus may be approached from the aorta or the pulmonary artery, depending on characteristics of the patient, the condition of the patient, and/or treating physician preference. Any of the methods described herein may further include advancing a delivery system, for example comprising a catheter or microcatheter, over the guidewire and through a length of the ductus and at least partially into a distal adjacent artery, for example the aorta or the pulmonary artery, depending on the approach selected. The guidewire is retracted through the delivery system while substantially maintaining a position of the delivery system in the ductus. Further, any of the method embodiments described herein may include loading a stent (any of the stent embodiments described herein) into a proximal end of the delivery system. Loading may include inserting a transfer sheath into a hub of the delivery system (e.g., a hub of the microcatheter or catheter); and advancing a pusherwire into the delivery system to transfer the stent (any of the stent embodiments described herein) into the delivery system (more specifically, a microcatheter or catheter of the delivery system). Any of the methods described herein may include advancing the stent (any of the stent embodiments described herein) through the delivery system until, for example a distal end of the stent approaches or reaches a distal tip or end of the microcatheter or catheter. Further, any of the methods described herein may include positioning a distal tip of the microcatheter or catheter at the distal end of the ductus arteriosus, and while substantially maintaining a position of the pusherwire, applying a reverse force to the microcatheter or catheter to deploy any of the stents described herein. The deployment, as described elsewhere herein, may be controlled such that the stent is deployed ring by ring, segment by segment, or set of segments by set of segments, or any combination thereof or an entire stent body is deployed substantially at once. The distal anchor or flange of the stent is unsheathed or deployed such that it is configured to engage the ostium of the adjacent vessel (e.g., aorta or pulmonary artery depending on approach). Any of the methods further include unsheathing the stent body and deploying the proximal anchor or flange of the stent at the ostium of the adjacent vessel (e.g., aorta or pulmonary artery depending on approach) to ensure end-to-end coverage of the ductus between the anchors with minimal protrusion into either of the aorta or the pulmonary artery. In some embodiments, any of the methods may include repositioning the stent during deployment or during distal anchoring (e.g., when the distal most segment, ring, or set of segments are deployed) and/or resheathing all or a portion of the stent during deployment.

Figure 4A:
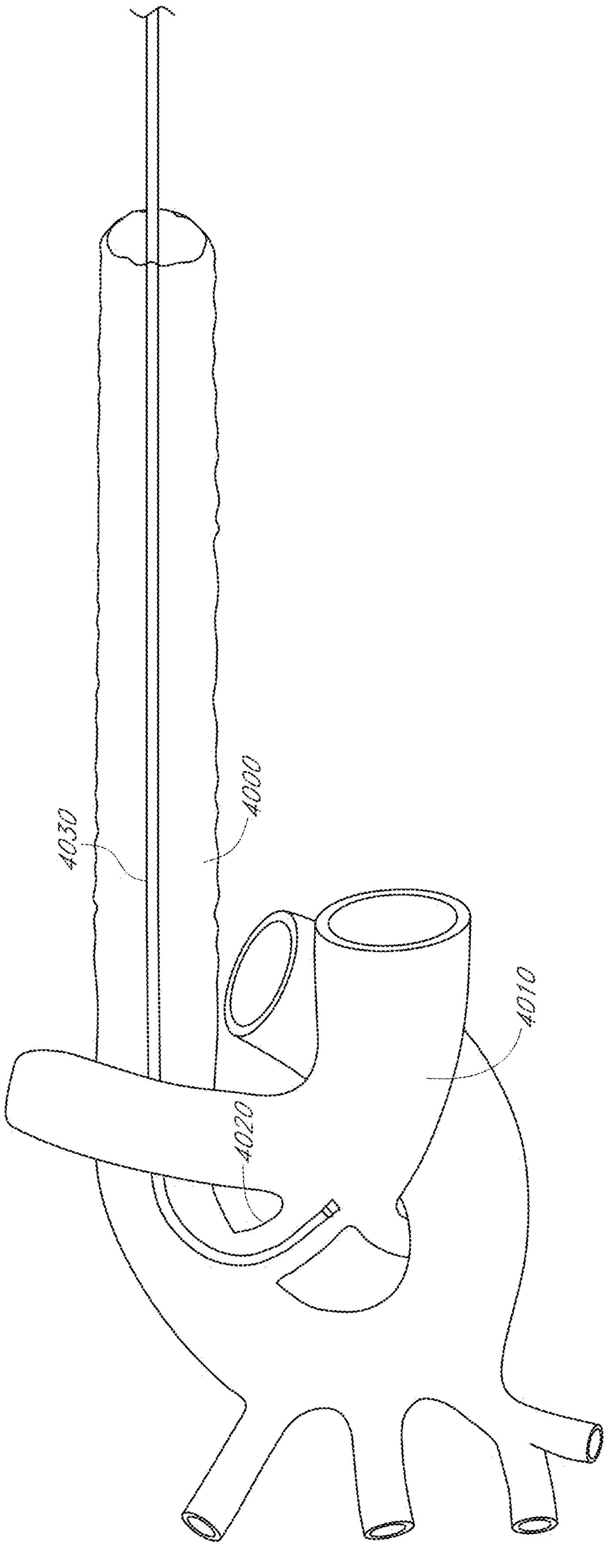
FIGS. 4A-4D show one embodiment of a method of maintaining a patent ductus arteriosus by approaching the ductus from the aorta.
Figure 4B:
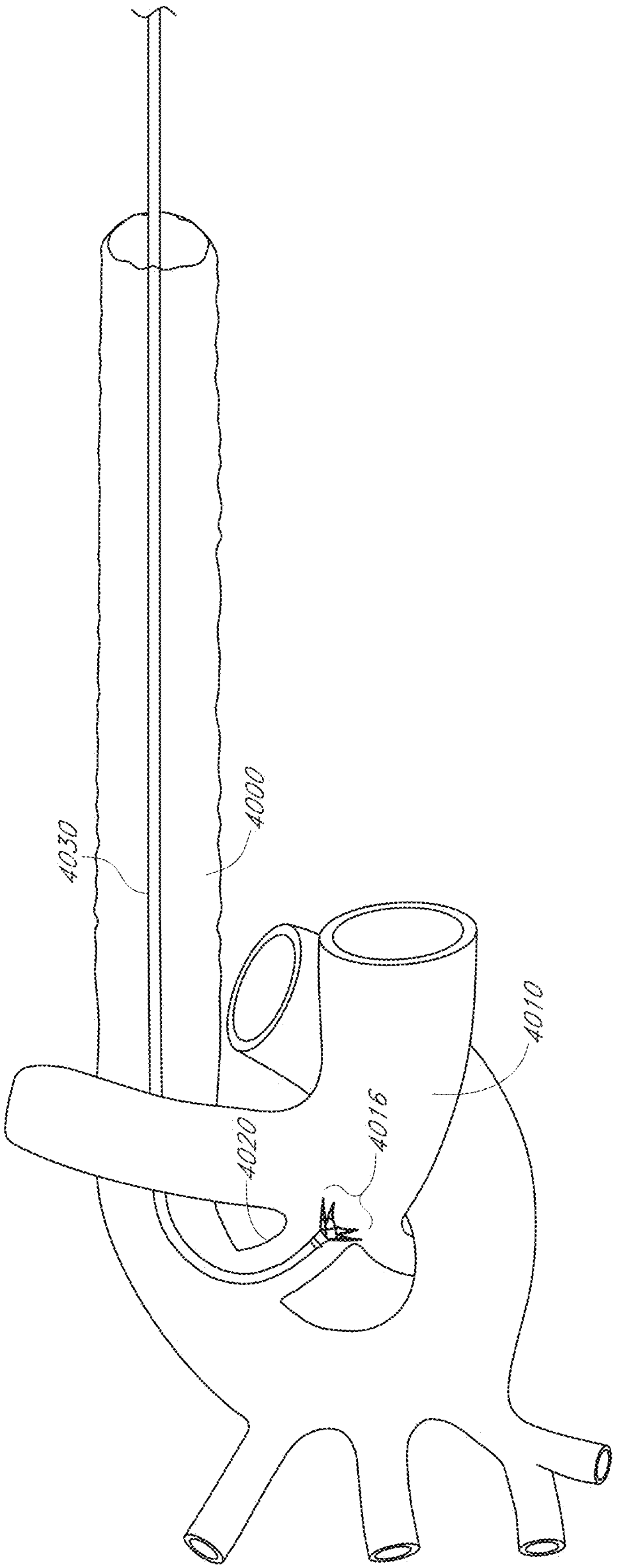
Figure 4C:
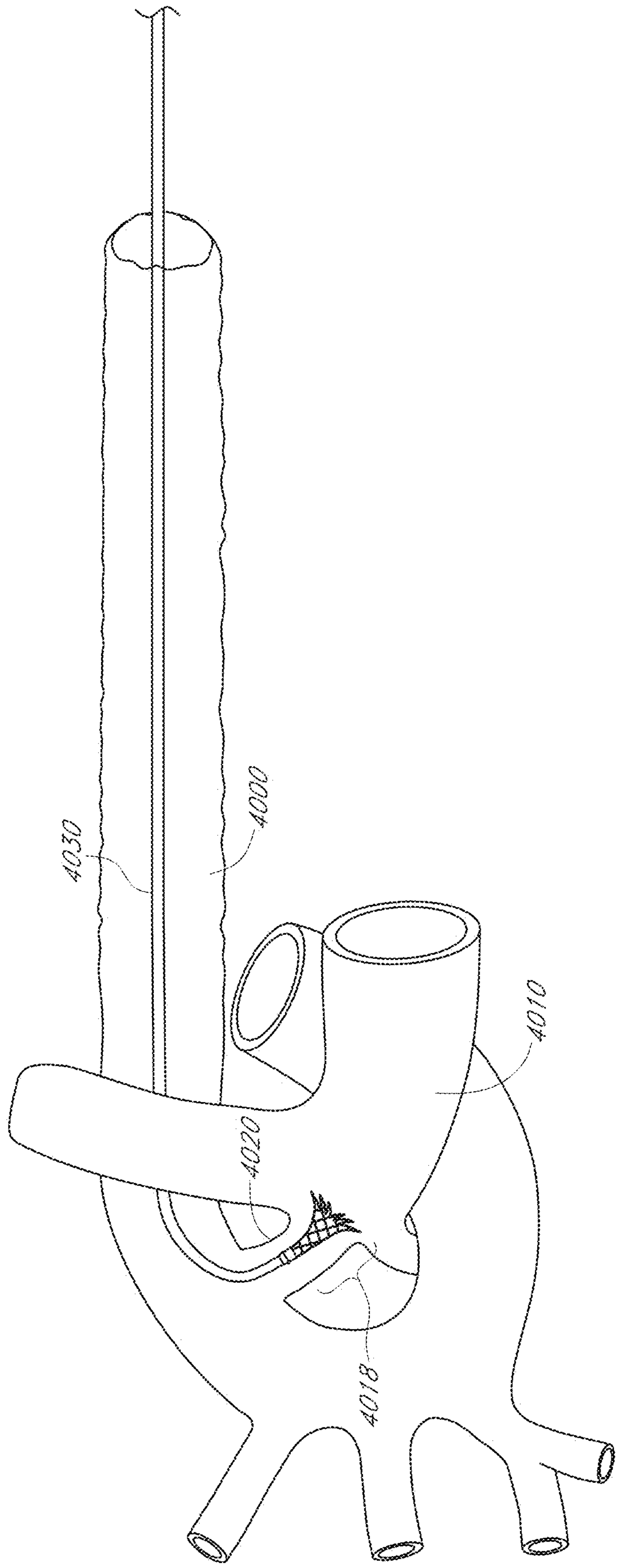
Figure 4D:
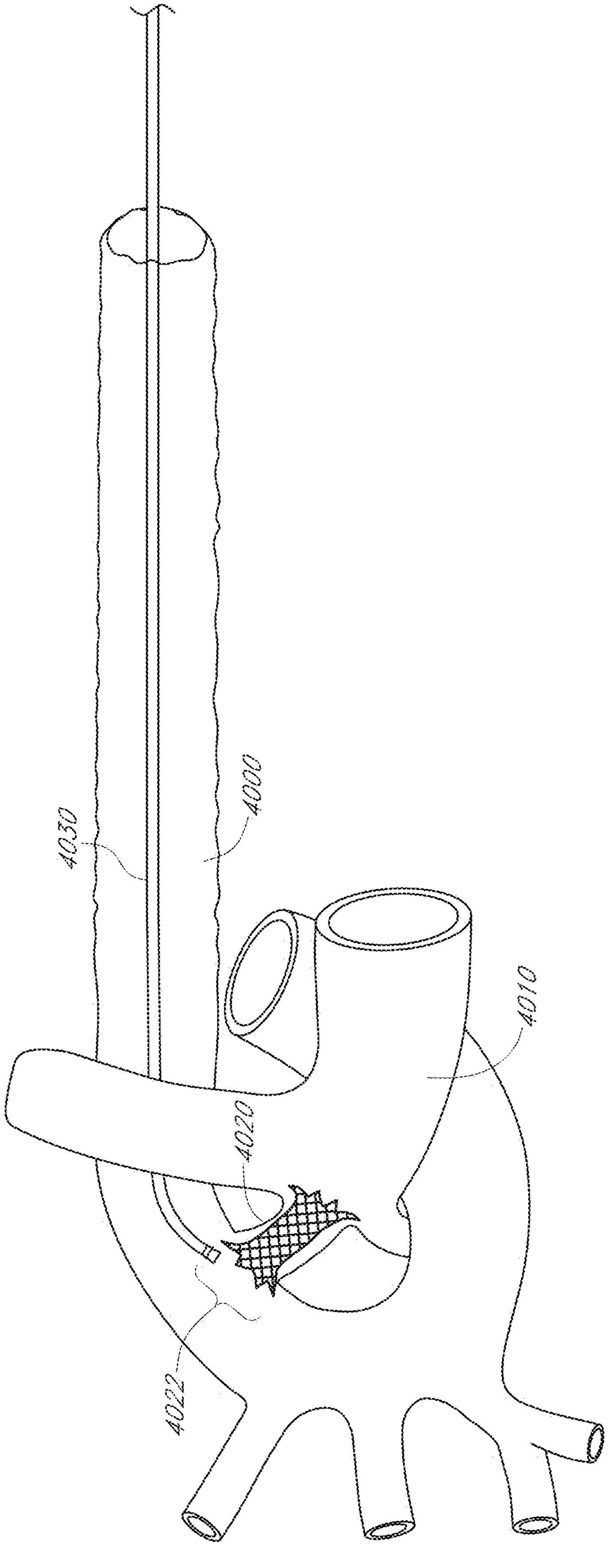

FIG. 4A illustrates an embodiment of a method of advancing a delivery system 4030 through an aorta 4000 and through a ductus arteriosus 4020 to approach a pulmonary artery 4010. As shown in FIG. 4B, the delivery system 4030 constrains a stent body, releases a first, or distal, flanged end 4016 that expands outwardly to the diameter or a fraction of the lumen of the ductus 4020. In some embodiments, the diameter of the stent is undersized relative to the diameter of the lumen defined by the ductus, for example, because of prostaglandin therapy or a selected size of the stent, as described elsewhere herein. The first flanged end 4016, which may comprise any one or more of the features shown in FIGS. 2A-2G of any of the stent embodiments described herein, at least partially anchors at the ductus lumen and/or at least partially circumferentially covers the ostium of the pulmonary artery 4010. The constrained stent body 4018 is released from the delivery system 4030, as shown in FIG. 4C. In some embodiments, constrained rings of a stent body are individually released, released segment by segment, released subset by subset (a subset comprising one or more segments), or released in aggregate from the distal end of the delivery system and expand until the entire length of the ductus is covered, and a second, or proximal, flanged end is released and expands outward. The second flanged end 4022 at least partially anchors at the lumen of the ductus 4020 and/or at least partially circumferentially covers the ostium of the aorta 4000, as shown in FIG. 4D. Advantageously, this method of delivering any of the stents described herein may be used to increase pulmonary circulation of the patient, but may also be used to increase systemic circulation.

Figure 5A:
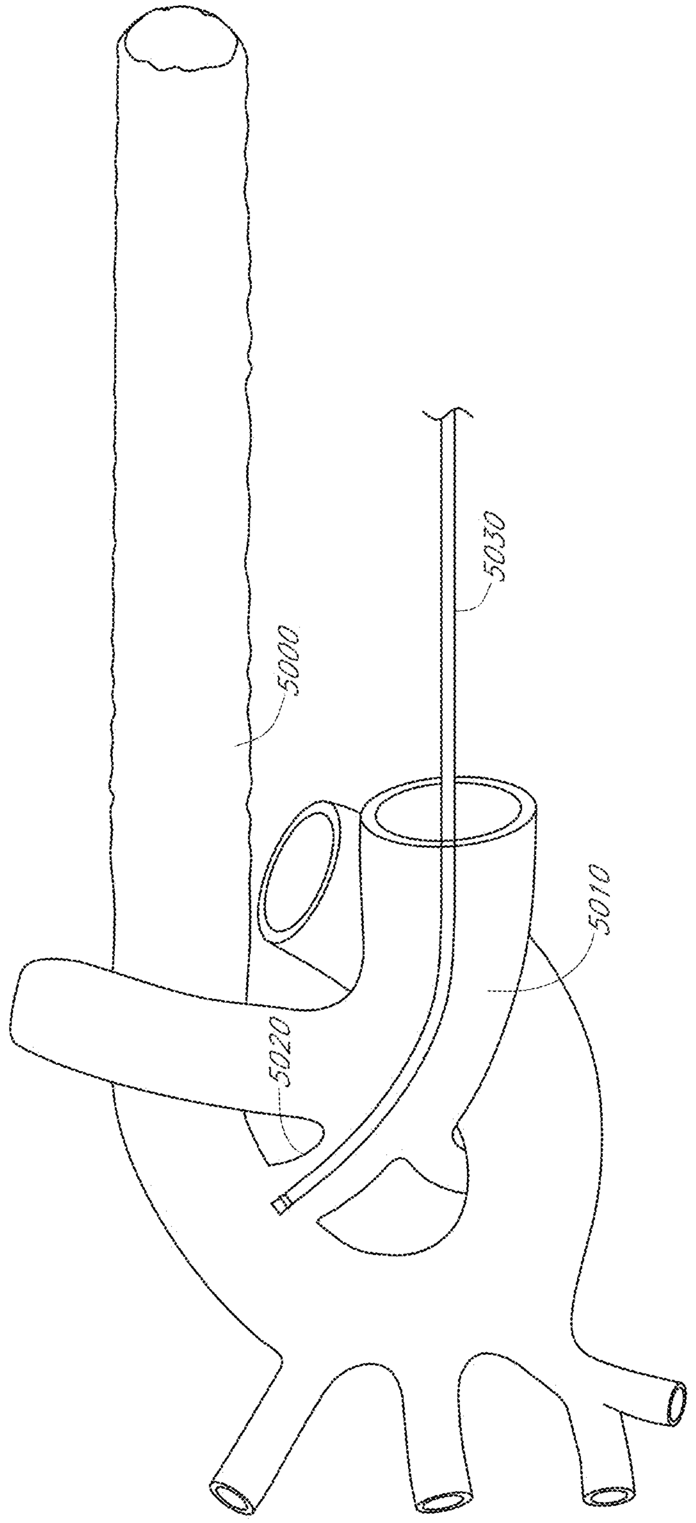
FIGS. 5A-5D show one embodiment of a method of maintaining a patent ductus arteriosus by approaching the ductus from the pulmonary artery.
Figure 5B:
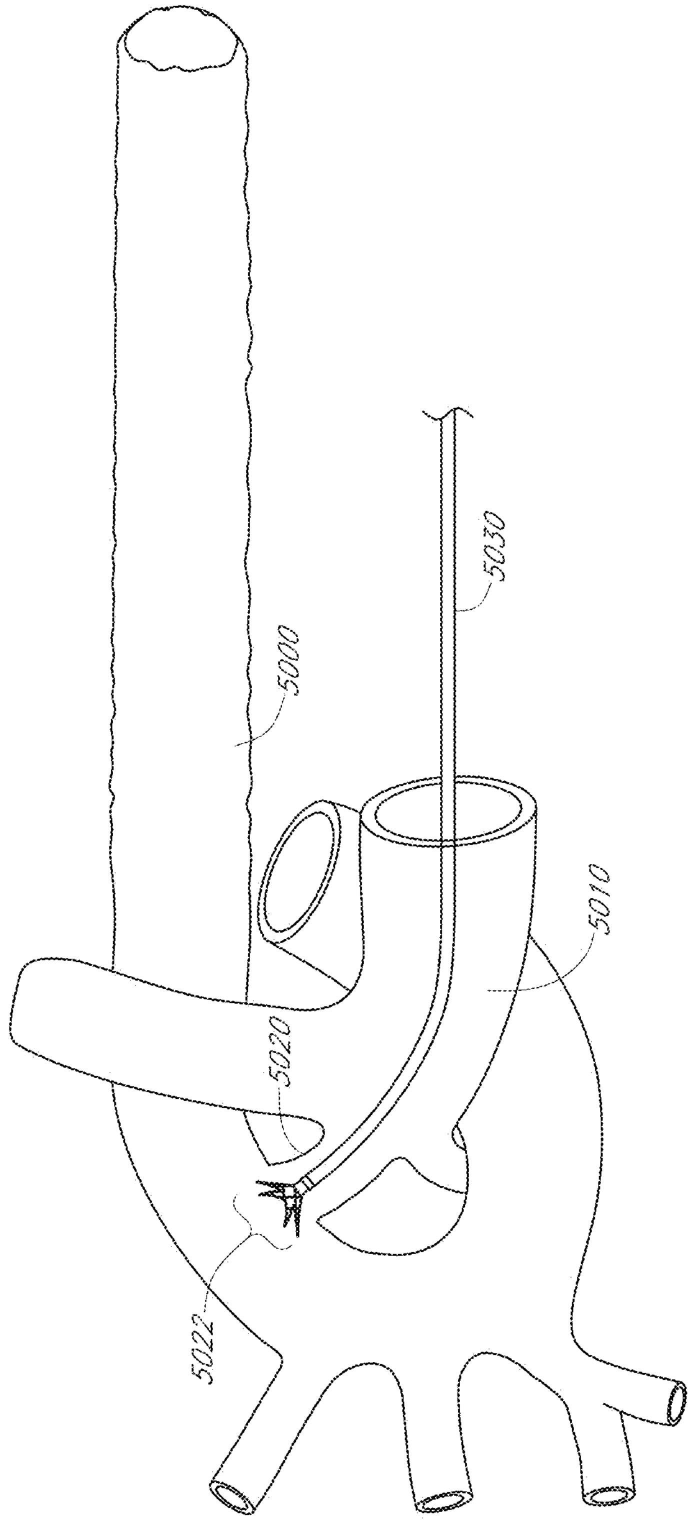
Figure 5C:
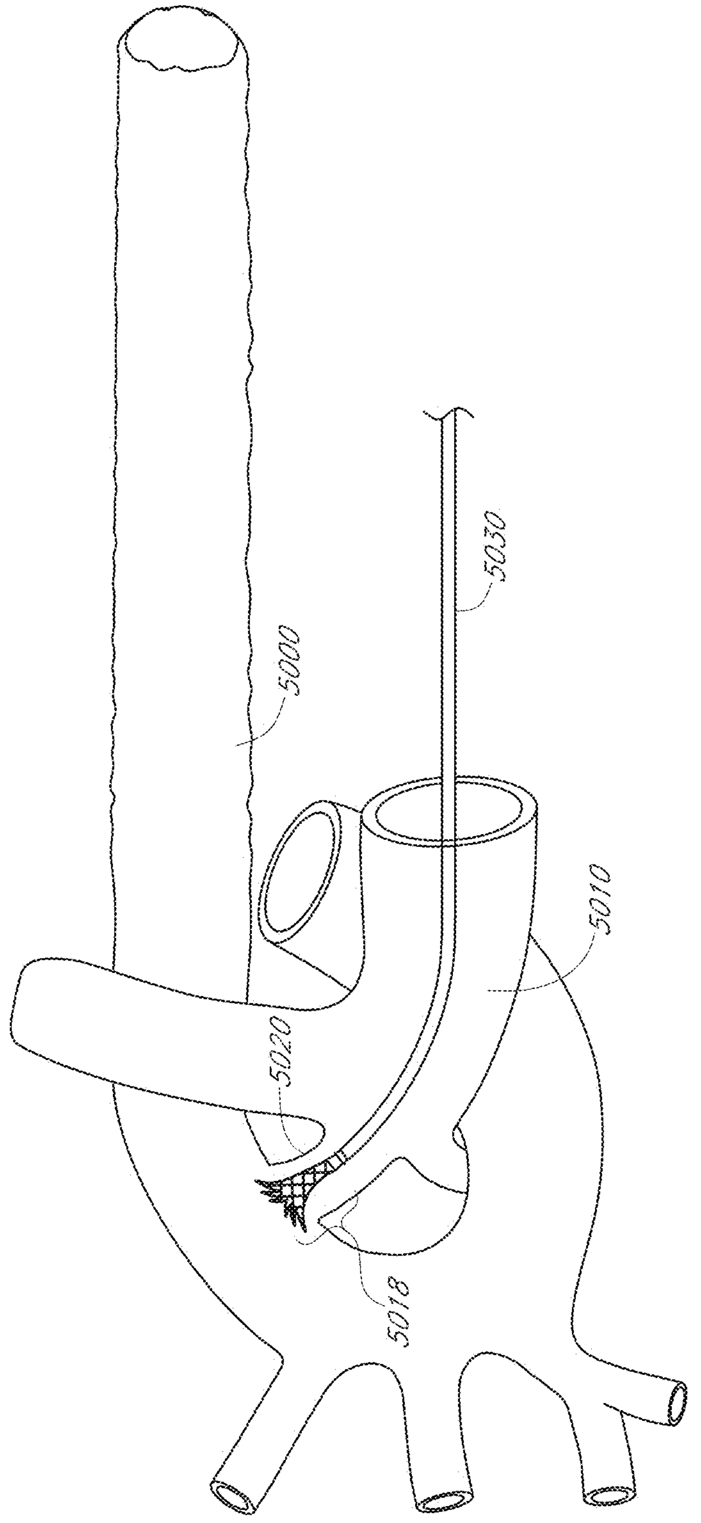
Figure 5D:
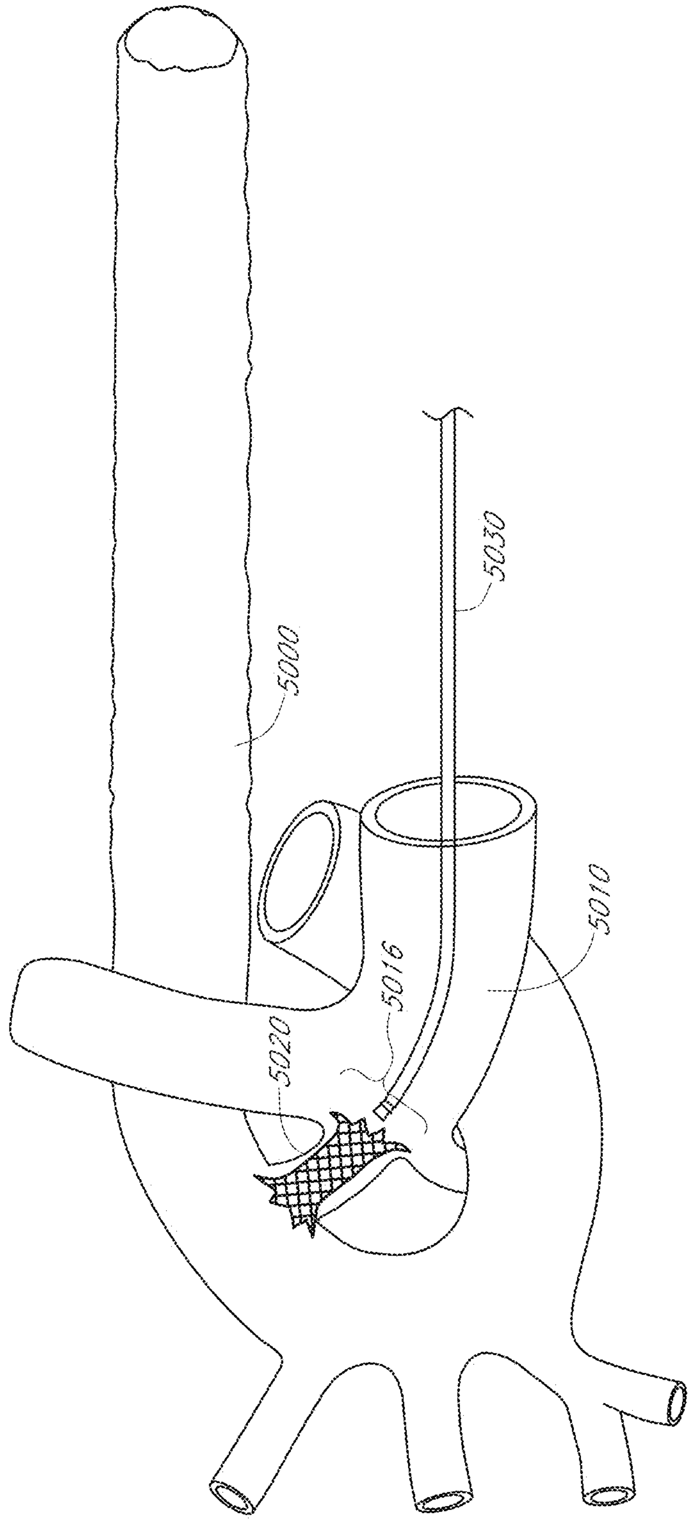

FIG. 5A illustrates an embodiment of a method of advancing a delivery system 5030 through the pulmonary artery 5010 and through a ductus arteriosus 5020 to approach an aorta 5000. As shown in FIG. 5B, the delivery system 5030 releases a first, or distal, flanged end 5022 that expands outwardly to the diameter or a fraction of the lumen of the ductus 5020. In some embodiments, the diameter of the stent is undersized relative to the diameter of the lumen defined by the ductus, for example, because of prostaglandin therapy or a selected size of the stent, as described elsewhere herein. The first flanged end 5022, which may comprise any of the features shown in FIGS. 2A-2G of any of the stent embodiments described herein, at least partially anchors at the ductus lumen and at least partially circumferentially covers the ostium of the aorta 5000. Constrained stent body 5018 is released from the delivery system 5030, as shown in FIG. 5C. In some embodiments, constrained rings are individually released from the distal end of the delivery system and expand until the entire length of the ductus 5020 is covered, and a second, or proximal, flanged end is released and expands outward. The second flanged end 5016 at least partially anchors at the lumen of the ductus 5020 and at least partially circumferentially covers the ostium of the pulmonary artery 5010, as shown in FIG. 5D. Advantageously, this method of delivery of any of the stents described herein increases systemic circulation of the patient, but may also be used to increase pulmonary circulation.

Figure 6A:
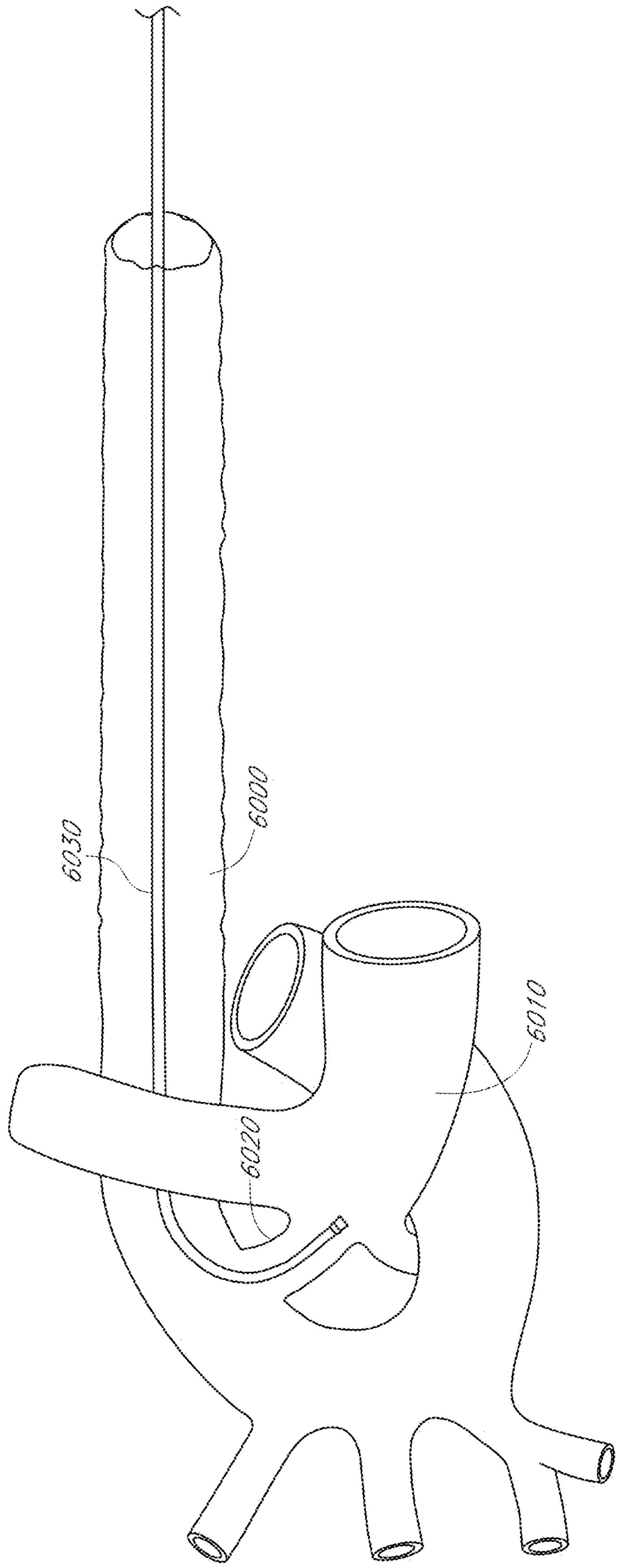
FIGS. 6A-6D show one embodiment of a method of maintaining a patent ductus arteriosus delivering a stent segment by segment.
Figure 6B:
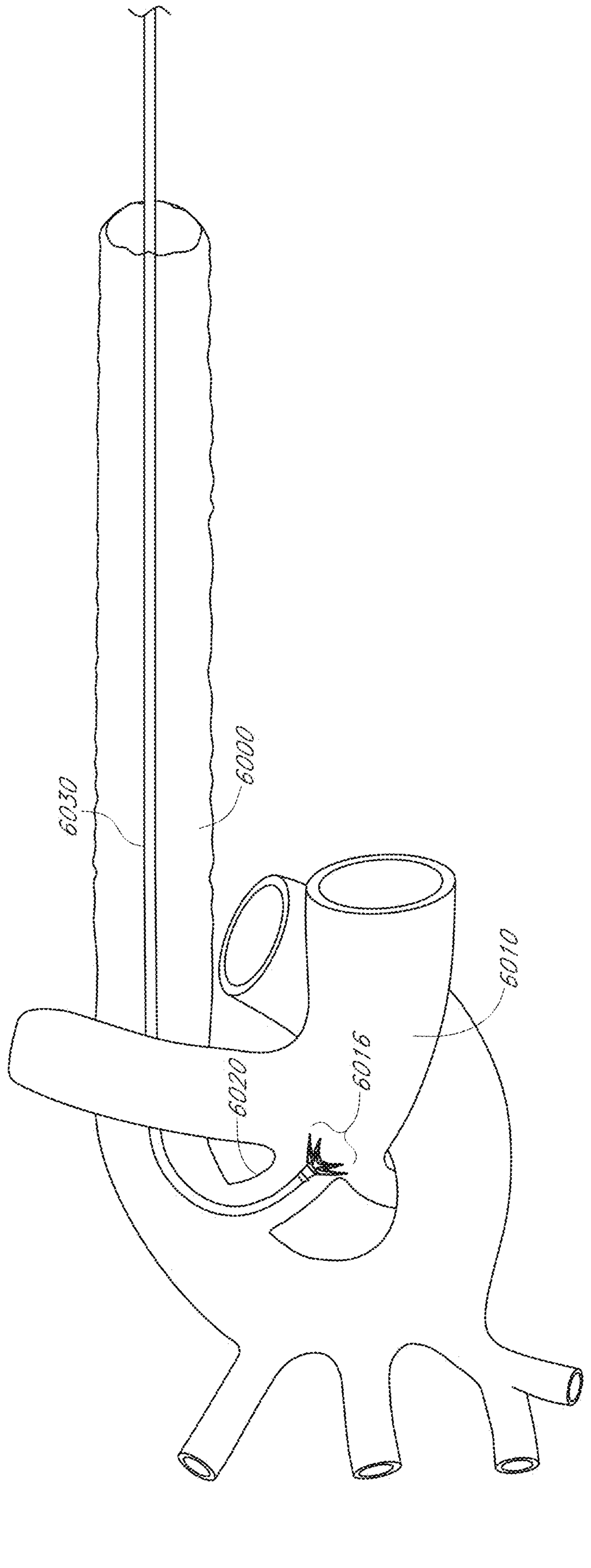
Figure 6C:
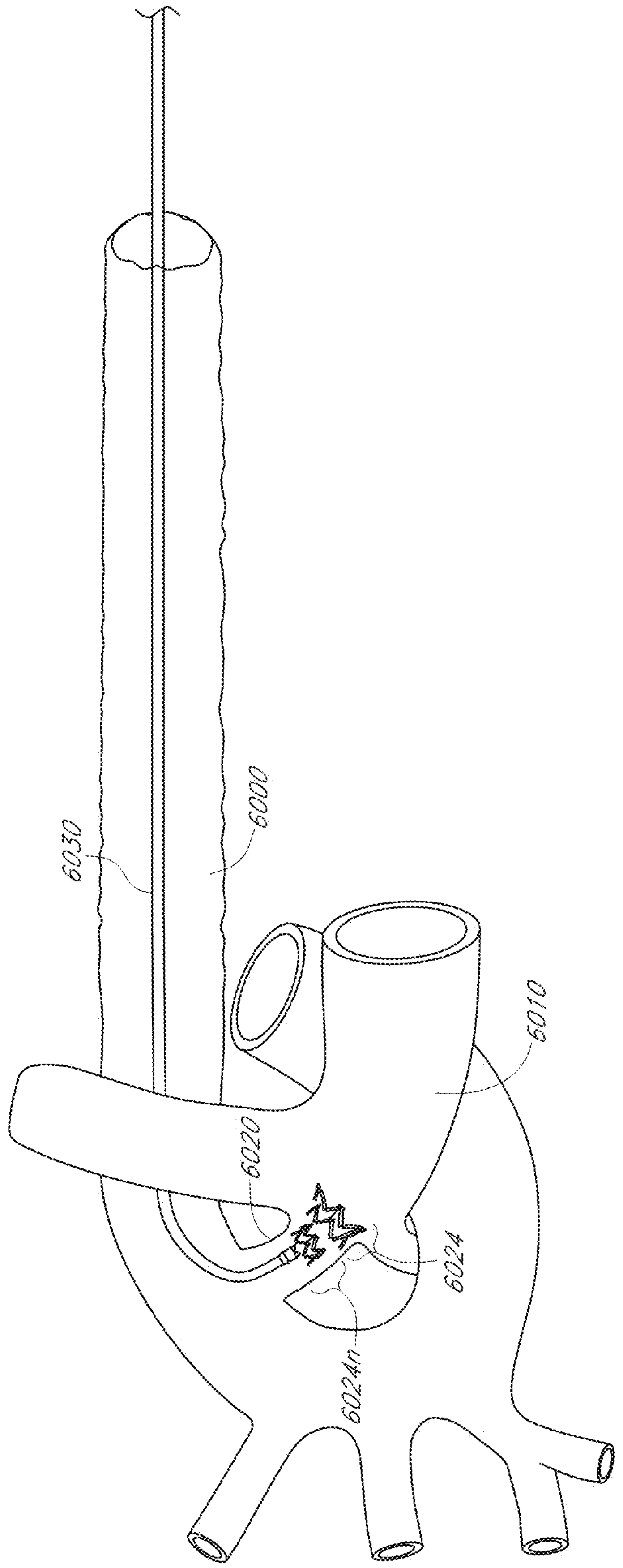
Figure 6D:
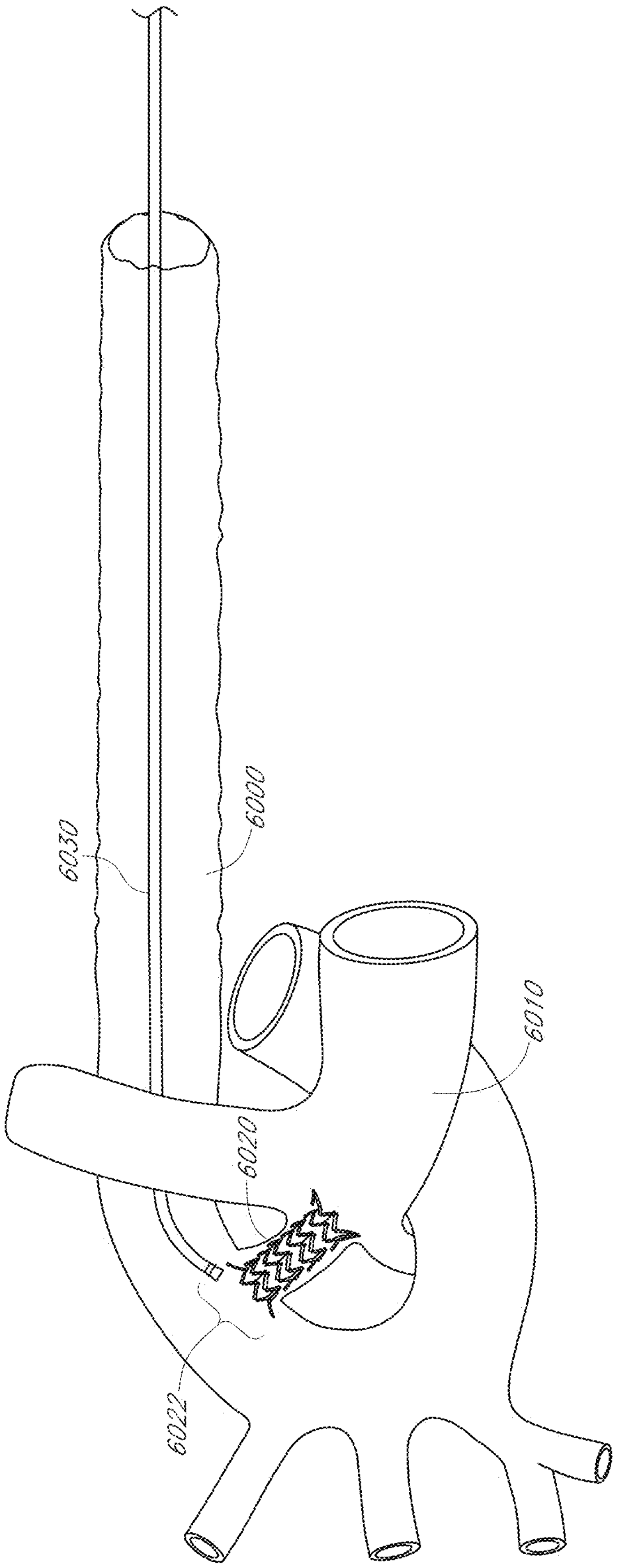

FIGS. 6A-6D illustrate an embodiment of a method that includes controllably and/or individually releasing segments of a stent using a delivery system 6030. As shown in FIG. 6A, the delivery system 6030 approaches the ductus arteriosus 6020 through aorta 6000 (but equally as likely through the pulmonary artery 6010) and advances through the length of the ductus 6020. When the delivery system 6030 reaches the opposite end of the ductus 6020, as shown in FIG. 6B, at either the pulmonary artery 6010 or aorta 6000, the microcatheter or catheter retracts while deploying a first, or distal, flanged end 6016 that anchors in the lumen of the ductus 6020 at the ostium of the artery (either pulmonary artery 6010 or aorta 6000 depending on approach). Further, as shown in FIG. 6C, the microcatheter or catheter (part of delivery system 6030) again retracts while deploying a first individual segment 6024 or a subset of segments 6024*n* that is coupled to the anchored first flanged end 6016. The microcatheter or catheter continues to retract while deploying additional coupled segments 6024*n* or a subset of a plurality of segments. It will be appreciated that additional segments may be controllably released individually or in sets (comprising more than one segment) until the entire length of the patient's ductus arteriosus 6020 is covered. Further, as discussed herein, each individual segment may include one or more rings that are coupled by one, one to two, one to three, or one to four connectors therebetween. The microcatheter or catheter may controllably retract a length while releasing one or more segments that is approximately the same length, a shorter length, or a longer length than each deployed segment or segments. In this manner, the deployment and release of the segments 6024*n* from the delivery system 6030 is adapted to match the anatomy of the ductus arteriosus 6020. Further, one end of one segment may be angled or offset in a nonparallel manner in relation to an adjacent segment to flexibly accommodate a curve or bend in the ductus 6020. The angled segments, such as shown at 236, 238 of FIG. 2F, is achieved by applying tension to one end of the microcatheter or catheter while pushing on the pusherwire to controllably release a set of segments or each segment of a set of segments along the length of the ductus 6020. Once the entire length of the ductus arteriosus 6020 is covered, the second, or proximal, flanged end 6022 is released and anchors at the second, or proximal, end of the ductus arteriosus 6020, as shown in FIG. 6D.

As discussed herein, an approximate number of segments within the delivery system may be selected and deployed based on the approximated length of the ductus arteriosus, where the number of segments may be of a slightly shorter or longer overall length as compared to the estimated or measured length of the ductus arteriosus. Advantageously, a distance between adjacent segments or a distance between rings within a segment may stretch or compress to ensure end-to-end coverage of the ductus or to ensure that the ductus is bracketed by the stent on each end of the ductus (pulmonary artery end and aorta end). More specifically, to stretch or shorten the overall length of the stent, the interventionalist or surgeon may control the length that the microcatheter or catheter retracts while releasing one or more segments. For example, to shorten the overall stent length, the microcatheter or catheter may retract a shorter length than the length of one or more coupled segments to reduce the length of the segments or between segments and the coupling connectors. When the second, or proximal, flanged end is anchored in an ostium of the opposite artery, the flanged ends retract towards one another as the segments and coupling connectors recover and return to their natural or biased state, thereby ensuring end to end coverage of the ductus by the stent. Alternatively, to lengthen the overall stent length, the microcatheter or catheter may retract a greater length than the length of one or more coupled segments to increase the length of the segments or between segments and the coupling connectors. When the second, or proximal, flanged end is anchored in an ostium of the opposite artery, the flanged ends oppose one another as the segments and coupling connectors return to their natural or biased state, thereby end to end coverage of the ductus by the stent. Further, the flanged ends of stretched or compressed segments and coupling connectors may also slightly or approximately compress or lengthen, respectively, the length of the ductus to ensure complete coverage of the ductus.

It will be appreciated that any of the stents described herein are made of or comprise a self-expanding shape memory alloy, such as, for example, copper-aluminium-nickel, nickel-titanium (i.e., Nitinol), iron-manganese-silicon, or copper-zinc-aluminium. The flexibility and stretchability of the material is conducive to ensuring access to and through a patient's tortuous anatomy while also having a radial outward force sufficient enough to support the surrounding tissue of the ductus arteriosus to ensure patency for at least about one month or longer when the patient no longer receives prostaglandins, at least in some embodiments.

In some embodiments, an outer diameter of the ductus arteriosus, when dilated with prostaglandins, ranges from between about 20% to about 50%; about 50% to about 100%; about 60% to about 120%; about 75% to about 140%; about 40% to about 140%; about 30% to about 100%; about 80% to about 120%; about 70% to about 110%; about 90% to about 150%; etc. larger than an outer diameter of any of the stents described herein, when in an expanded, deployed configuration.

Further, in some embodiments, an outer diameter of the ductus arteriosus is larger than an outer diameter of any of the stents described herein, when in an expanded, deployed configuration in a range of between about 30% to about 55%; about 10% to about 35%; etc.

Any of the stent embodiments described herein may range in an outer diameter of about 3 mm to about 4.5 mm or about 5 mm and sized to a ductus having a diameter of about 4 mm to about 8 mm, for example for ductal dependent pulmonary circulation, depending on the patient anatomy and size. Any of the stent embodiments described herein may range in an outer diameter of about 6 mm to about 10 mm and sized to a ductus having a diameter of about 5 mm to about 9 mm, for example for ductal dependent systemic circulation, depending on patient anatomy and size.

Further, the anchoring ends that anchor at the ostia advantageously do not significantly extend into or block the aortic or pulmonary arteries. As discussed herein, some embodiments of the anchoring ends do not extend into the adjacent or connecting arteries by more than about 0 mm, more than about 0.25 mm, more than about 0.5 mm, more than about 1 mm, more than about 2 mm; or by more than between about 0.5 mm and 2.5 mm, about 0.25 mm to about 2.5 mm; about 1 mm to about 2 mm, about 1.5 mm to about 2.5 mm, etc.

Embodiments of the stent delivery system can use laser-cut hypotube technology that allows for thinner stent body design, seamless transition zones, and greater flexibility of the stent with a lower kink radius than standard braided or mesh configurations. The delivery system can be configured to fit through a 4F or 5F catheter or microcatheter to minimize iatrogenic vessel damage. In some embodiments, the delivery system enables access via femoral, carotid, or axillary arteries, as a patient's ductus arteriosus may need to be accessed from any one of those vessels. The delivery system can be configured to track over existing guidewires through a ductus arteriosus that undergoes more than one full 360 degree turn (Type III ductus tortuosity index, shown in FIG. 1C). As noted above, the stents are designed uniquely for neonatal and pediatric ductus arteriosus stenting to overcome the anatomical challenges of their small, tortuous vessels, while enabling placement of a properly sized stent from end-to-end of the ductus without protrusion into the surrounding vessels.

As noted above, embodiments of stents described herein can be made by laser-cutting hypotubes and shape setting to achieve the desired radial force and flexibility. Testing using anatomical modeling can provide a deeper understanding of the biomechanical forces affecting the ductus arteriosus, resulting in better stent designs ensuring both safety and durability. For example, the assessment of physiologic motion of the ductus arteriosus during the cardiac and respiratory cycle informs how any of the stent segments described herein move relative to one another and how the anchoring ends of any of the stent designs described herein interact with the walls of the aorta and the pulmonary vessels.

For any of the stent embodiments described herein, stent flexibility may be increased by reducing connecting member width, for example. Additionally, or alternatively, any of the stent embodiments described herein may be treated with regioselective heat and/or regioselective wall thickness removal (either by selective bead-blasting or masked chem-etching) to increase flexibility of the stent. Additionally, or alternatively, one or more of a stiffness, size, longitudinal angle, or circumferential angle of the anchoring ends are adjustable by altering a strut thickness, length, and/or heat shaping parameters as well as other levers described above to tune the level of engagement of the anchors with the vessel wall and amount of force they exert on the vessel walls. Further, any of the stent embodiments described herein may be heat shaped to create varying curves and angles without requiring alterations to the laser cut patterns.

In some embodiments, any of the stents described herein may comprise any one or more of the following coatings or sleeves on an inner diameter, outer diameter, or along an entire length of the device (inner and outer diameter): an anti-thrombogenic, anti-restenotic, lubricious, etc.

In some embodiments, the stents described herein are (1) able to be manufactured in diameters from about 3 mm to about 5 mm or about 6 mm to about 10 mm in about 0.5 mm increments, (2) deliverable through a 4F or 5F catheter or microcatheter (e.g., 2.4F to 2.8F), and (3) have a radial force sufficient to maintain ductus patency. In some embodiments, any of the stents described herein can additionally, or alternatively, completely cover (within 1 mm) a majority of ductus anatomies, for example, those that have an undilated diameter of about 4 mm to about 6 mm, for ductal dependent pulmonary circulation, or an undilated diameter of about 4 mm to about 9 mm, for ductal dependent systemic circulation, and a length ranging from about 8 mm to about 28 mm (+/−about 4 mm), without extending into either the aorta or the pulmonary arteries by more than about 1 mm or about 2 mm.

Any of the stents and methods described herein may be configured to treat any of the three major ductal anatomies encountered in ductal dependent pulmonary circulation, for example Type I (i.e., straight, FIG. 1A), Type II (i.e., some tortuosity, FIG. 1B), and Type III (i.e., curves greater than 360 degrees, FIG. 1C), and ductal anatomies encountered in ductal dependent systemic circulation.

When a feature or element is herein referred to as being "on" another feature or element, it can be directly on the other feature or element or intervening features and/or elements may also be present. In contrast, when a feature or element is referred to as being "directly on" another feature or element, there are no intervening features or elements present. It will also be understood that, when a feature or element is referred to as being "connected", "attached" or "coupled" to another feature or element, it can be directly connected, attached or coupled to the other feature or element or intervening features or elements may be present. In contrast, when a feature or element is referred to as being "directly connected", "directly attached" or "directly coupled" to another feature or element, there are no intervening features or elements present. Although described or shown with respect to one embodiment, the features and elements so described or shown can apply to other embodiments. It will also be appreciated by those of skill in the art that references to a structure or feature that is disposed "adjacent" another feature may have portions that overlap or underlie the adjacent feature.

Terminology used herein is for the purpose of describing particular embodiments only and is not intended to be limiting of the invention. For example, as used herein, the singular forms "a", "an" and "the" are intended to include the plural forms as well, unless the context clearly indicates otherwise. It will be further understood that the terms "comprises" and/or "comprising," when used in this specification, specify the presence of stated features, steps, operations, elements, and/or components, but do not preclude the presence or addition of one or more other features, steps, operations, elements, components, and/or groups thereof. As used herein, the term "and/or" includes any and all combinations of one or more of the associated listed items and may be abbreviated as "/".

Spatially relative terms, such as "under", "below", "lower", "over", "upper" and the like, may be used herein for ease of description to describe one element or feature's relationship to another element(s) or feature(s) as illustrated in the figures. It will be understood that the spatially relative terms are intended to encompass different orientations of the device in use or operation in addition to the orientation depicted in the figures. For example, if a device in the figures is inverted, elements described as "under" or "beneath" other elements or features would then be oriented "over" the other elements or features. Thus, the exemplary term "under" can encompass both an orientation of over and under. The device may be otherwise oriented (rotated 90 degrees or at other orientations) and the spatially relative descriptors used herein interpreted accordingly. Similarly, the terms "upwardly", "downwardly", "vertical", "horizontal" and the like are used herein for the purpose of explanation only unless specifically indicated otherwise.

Although the terms "first" and "second" may be used herein to describe various features/elements (including steps), these features/elements should not be limited by these terms, unless the context indicates otherwise. These terms may be used to distinguish one feature/element from another feature/element. Thus, a first feature/element discussed below could be termed a second feature/element, and similarly, a second feature/element discussed below could be termed a first feature/element without departing from the teachings of the present invention.

Throughout this specification and the claims which follow, unless the context requires otherwise, the word "comprise", and variations such as "comprises" and "comprising" means various components can be co-jointly employed in the methods and articles (e.g., compositions and apparatuses including device and methods). For example, the term "comprising" will be understood to imply the inclusion of any stated elements or steps but not the exclusion of any other elements or steps.

As used herein in the specification and claims, including as used in the examples and unless otherwise expressly specified, all numbers may be read as if prefaced by the word "about" or "approximately," even if the term does not expressly appear. The phrase "about" or "approximately" may be used when describing magnitude and/or position to indicate that the value and/or position described is within a reasonable expected range of values and/or positions. For example, a numeric value may have a value that is +/−0.1% of the stated value (or range of values), +/−1% of the stated value (or range of values), +/−2% of the stated value (or range of values), +/−5% of the stated value (or range of values), +/−10% of the stated value (or range of values), etc. Any numerical values given herein should also be understood to include about or approximately that value, unless the context indicates otherwise. For example, if the value "10" is disclosed, then "about 10" is also disclosed. Any numerical range recited herein is intended to include all sub-ranges subsumed therein. It is also understood that when a value is disclosed that "less than or equal to" the value, "greater than or equal to the value" and possible ranges between values are also disclosed, as appropriately understood by the skilled artisan. For example, if the value "X" is disclosed the "less than or equal to X" as well as "greater than or equal to X" (e.g., where X is a numerical value) is also disclosed. It is also understood that [the] throughout the application, data is provided in a number of different formats, and that this data, represents endpoints and starting points, and ranges for any combination of the data points. For example, if a particular data point "10" and a particular data point "15" are disclosed, it is understood that greater than, greater than or equal to, less than, less than or equal to, and equal to 10 and 15 are considered disclosed as well as between 10 and 15. It is also understood that each unit between two particular units are also disclosed. For example, if 10 and 15 are disclosed, then 11, 12, 13, and 14 are also disclosed.

Although various illustrative embodiments are described above, any of a number of changes may be made to various embodiments without departing from the scope of the invention as described by the claims. For example, the order in which various described method steps are performed may often be changed in alternative embodiments, and in other alternative embodiments one or more method steps may be skipped altogether. Optional features of various device and system embodiments may be included in some embodiments and not in others. Therefore, the foregoing description is provided primarily for exemplary purposes and should not be interpreted to limit the scope of the invention as it is set forth in the claims.

The examples and illustrations included herein show, by way of illustration and not of limitation, specific embodiments in which the subject matter may be practiced. As mentioned, other embodiments may be utilized and derived there from, such that structural and logical substitutions and changes may be made without departing from the scope of this disclosure. Such embodiments of the inventive subject matter may be referred to herein individually or collectively by the term "invention" merely for convenience and without intending to voluntarily limit the scope of this application to any single invention or inventive concept, if more than one is, in fact, disclosed. Thus, although specific embodiments have been illustrated and described herein, any arrangement calculated to achieve the same purpose may be substituted for the specific embodiments shown. This disclosure is intended to cover any and all adaptations or variations of various embodiments. Combinations of the above embodiments, and other embodiments not specifically described herein, will be apparent to those of skill in the art upon reviewing the above description.

The invention claimed is:

1. A method of maintaining a patent ductus arteriosus in a pediatric patient, comprising:

administering a prostaglandin to the pediatric patient to dilate a lumen defined by a ductus arteriosus of the pediatric patient;

deploying a first end of a self-expanding stent at a first end of the lumen defined by the ductus arteriosus, wherein a stent body of the self-expanding stent comprises a plurality of rings, and has three or fewer connections between adjacent rings of the plurality of rings;

anchoring at least a portion of a first flange of the first end of the self-expanding stent such that the first flange at least partially circumferentially covers one of: a pulmonary artery ostium or an aortic ostium;

deploying a second end of the self-expanding stent, such that the stent body covers an entire length of the lumen defined by the ductus arteriosus;

anchoring at least a portion of a second flange of the second end of the self-expanding stent such that the second flange at least partially circumferentially covers the other of the pulmonary artery ostium or the aortic ostium; and causing controlled blood flow in a pulmonary circulation of the pediatric patient having ductal-dependent pulmonary circulation.

2. The method of claim 1, further comprising deploying the stent body segment by segment to control a spacing between adjacent segments to ensure coverage of the entire length of the lumen defined by the ductus arteriosus.

3. The method of claim 2, wherein the stent body has two or fewer connections between the adjacent rings of the plurality of rings.

4. The method of claim 2, wherein the stent body has zero or one connection between the adjacent rings of the plurality of rings.

5. The method of claim 2, wherein a segment comprises one of: a ring or a ring and a connector.

6. The method of claim 1, wherein each of the first end and the second end of the self-expanding stent is about 20% to about 40% larger than a diameter of the stent body after deployment.

7. The method of claim 1, wherein at least a portion of a diameter of the lumen defined by the ductus arteriosus is about 20% to about 140% larger than an outer diameter of the stent body of the self-expanding stent after deployment.

8. The method of claim 1, further comprising applying tension or compression to the stent body to cover the entire length of the lumen of the ductus arteriosus.

* * * * *